United States Patent
Biggs et al.

(10) Patent No.: US 7,837,679 B2
(45) Date of Patent: Nov. 23, 2010

(54) CONTROL SYSTEM AND PROCESS FOR APPLICATION OF ENERGY TO AIRWAY WALLS AND OTHER MEDIUMS

(75) Inventors: Michael Biggs, Denver, CO (US); Roger A. Stern, Cupertino, CA (US); Christopher J. Danek, San Carlos, CA (US)

(73) Assignee: Asthmatx, Inc., Sunnyvale, CA (US)

(*) Notice: Subject to any disclaimer, the term of this patent is extended or adjusted under 35 U.S.C. 154(b) by 1087 days.

(21) Appl. No.: 11/458,084

(22) Filed: Jul. 17, 2006

(65) Prior Publication Data

US 2006/0247727 A1    Nov. 2, 2006

Related U.S. Application Data

(60) Division of application No. 10/414,411, filed on Apr. 14, 2003, now Pat. No. 7,104,987, which is a continuation of application No. PCT/US01/32321, filed on Oct. 17, 2001, and a continuation-in-part of application No. PCT/US00/28745, filed on Oct. 17, 2000.

(51) Int. Cl.
*A61B 18/10* (2006.01)

(52) U.S. Cl. .................. 606/34; 607/102; 606/41

(58) Field of Classification Search ............. 606/32–35, 606/41, 48–50; 607/101–102
See application file for complete search history.

(56) References Cited

U.S. PATENT DOCUMENTS 612,724 A   10/1898   Hamilton (Continued)

FOREIGN PATENT DOCUMENTS

DE    19529634 A1    2/1997

(Continued)

OTHER PUBLICATIONS

An S. S., et al., "Airway smooth muscle dynamics: a common pathway of airway obstruction in asthma," European Respiratory Journal, 2007, 29 (5), 834-860.

(Continued)

*Primary Examiner*—Michael Peffley
(74) *Attorney, Agent, or Firm*—Perkins Coie LLP

(57) ABSTRACT

The present invention includes a system for delivering energy to an airway wall of a lung comprising an energy delivering apparatus and a PID controller having one or more variable gain factors which are rest after energy deliver has begun. The energy delivering apparatus may include a flexible elongated member and a distal expandable basket having at least one electrode for transferring energy to the airway wall and at least one temperature sensor for measuring temperature. The PID controller determines a new power set point base on an error between a preset temperature and the measured temperature. The algorithm can be $P_{i+1}=P_i+G(\alpha e_i+\beta e_{i-1}+\gamma e_{i-2})$ where $\alpha$, $\beta$ and $\gamma$ are preset values and $\alpha$ is from 1 to 2; $\beta$ is from −1 to −2; and $\gamma$ is from −0.5 to 0-5. In another variation, the controller is configured to shut down if various measured parameters are exceeded such as, for example, energy, impedance, temperature, temperature differences, activation time and combinations thereof. Methods for treating a target medium using a PID algorithm are also provided.

53 Claims, 5 Drawing Sheets

U.S. PATENT DOCUMENTS

| | | |
|---|---|---|
| 1,155,169 A | 9/1915 | Starkweather |
| 1,207,479 A | 12/1916 | Bisgaard |
| 1,216,183 A | 2/1917 | Swingle |
| 2,072,346 A | 3/1937 | Smith |
| 3,320,957 A | 5/1967 | Sokolik |
| 3,568,659 A | 3/1971 | Karnegis |
| 3,667,476 A | 6/1972 | Muller |
| 3,692,029 A | 9/1972 | Adair |
| 3,995,617 A | 12/1976 | Watkins et al. |
| 4,095,602 A | 6/1978 | Leveen |
| 4,116,589 A | 9/1978 | Rishton |
| 4,129,129 A | 12/1978 | Amrine |
| 4,154,246 A | 5/1979 | Leveen |
| 4,461,283 A | 7/1984 | Doi |
| 4,502,490 A | 3/1985 | Evans et al. |
| 4,503,855 A | 3/1985 | Maslanka |
| 4,512,762 A | 4/1985 | Spears |
| 4,522,212 A | 6/1985 | Gelinas et al. |
| 4,557,272 A | 12/1985 | Carr |
| 4,565,200 A | 1/1986 | Cosman |
| 4,567,882 A | 2/1986 | Heller |
| 4,584,998 A | 4/1986 | McGrail |
| 4,612,934 A | 9/1986 | Borkan |
| 4,621,642 A | 11/1986 | Chen |
| 4,621,882 A | 11/1986 | Krumme |
| 4,625,712 A | 12/1986 | Wampler |
| 4,643,186 A | 2/1987 | Rosen et al. |
| 4,646,737 A | 3/1987 | Hussein et al. |
| 4,674,497 A | 6/1987 | Ogasawara |
| 4,683,890 A | 8/1987 | Hewson |
| 4,704,121 A | 11/1987 | Moise |
| 4,706,688 A | 11/1987 | Don Michael et al. |
| 4,709,698 A | 12/1987 | Johnston et al. |
| 4,739,759 A | 4/1988 | Rexroth et al. |
| 4,754,065 A | 6/1988 | Levenson et al. |
| 4,754,752 A | 7/1988 | Ginsburg et al. |
| 4,765,959 A | 8/1988 | Fukasawa |
| 4,772,112 A | 9/1988 | Zider et al. |
| 4,773,899 A | 9/1988 | Spears |
| 4,779,614 A | 10/1988 | Moise |
| 4,784,135 A | 11/1988 | Blum et al. |
| 4,790,305 A | 12/1988 | Zoltan et al. |
| 4,799,479 A | 1/1989 | Spears |
| 4,802,492 A | 2/1989 | Grunstein |
| 4,817,586 A | 4/1989 | Wampler |
| 4,825,871 A | 5/1989 | Cansell |
| 4,827,935 A | 5/1989 | Geddes et al. |
| 4,846,152 A | 7/1989 | Wampler et al. |
| 4,862,886 A | 9/1989 | Clarke et al. |
| 4,895,557 A | 1/1990 | Moise et al. |
| 4,906,229 A | 3/1990 | Wampler |
| 4,907,589 A | 3/1990 | Cosman |
| 4,908,012 A | 3/1990 | Moise et al. |
| 4,920,978 A | 5/1990 | Colvin |
| 4,944,722 A | 7/1990 | Carriker et al. |
| 4,955,377 A | 9/1990 | Lennox et al. |
| 4,967,765 A | 11/1990 | Turner et al. |
| 4,969,865 A | 11/1990 | Hwang et al. |
| 4,976,709 A | 12/1990 | Sand |
| 4,985,014 A | 1/1991 | Orejola |
| 4,991,603 A | 2/1991 | Cohen et al. |
| 5,009,636 A | 4/1991 | Wortley et al. |
| 5,009,936 A | 4/1991 | Yamanaka et al. |
| 5,010,892 A | 4/1991 | Colvin et al. |
| 5,019,075 A | 5/1991 | Spears et al. |
| 5,027,829 A | 7/1991 | Larsen |
| 5,030,645 A | 7/1991 | Kollonitsch |
| 5,036,848 A | 8/1991 | Hewson |
| 5,053,033 A | 10/1991 | Clarke |
| 5,056,519 A | 10/1991 | Vince |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,105,826 A | 4/1992 | Smits et al. |
| 5,106,360 A | 4/1992 | Ishiwara et al. |
| 5,107,830 A | 4/1992 | Younes |
| 5,114,423 A | 5/1992 | Kasprzyk et al. |
| 5,116,864 A | 5/1992 | March et al. |
| 5,117,828 A | 6/1992 | Metzger et al. |
| 5,135,517 A | 8/1992 | McCoy |
| 5,152,286 A | 10/1992 | Sitko et al. |
| 5,165,420 A | 11/1992 | Strickland |
| 5,167,223 A | 12/1992 | Koros et al. |
| 5,170,803 A | 12/1992 | Hewson et al. |
| 5,174,288 A | 12/1992 | Bardy et al. |
| 5,188,602 A | 2/1993 | Nichols |
| 5,191,883 A | 3/1993 | Lennox et al. |
| 5,213,576 A | 5/1993 | Abiuso et al. |
| 5,215,103 A | 6/1993 | Desai |
| 5,231,996 A | 8/1993 | Bardy et al. |
| 5,232,444 A | 8/1993 | Just et al. |
| 5,234,456 A | 8/1993 | Silvestrini |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,292,331 A | 3/1994 | Boneau |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,343,936 A | 9/1994 | Beatenbough et al. |
| 5,345,936 A | 9/1994 | Pomeranz et al. |
| 5,366,443 A | 11/1994 | Eggers et al. |
| 5,368,591 A | 11/1994 | Lennox et al. |
| 5,370,644 A | 12/1994 | Langberg |
| 5,370,679 A | 12/1994 | Atlee, III |
| 5,374,287 A | 12/1994 | Rubin |
| 5,383,917 A | 1/1995 | Desai et al. |
| 5,393,207 A | 2/1995 | Maher et al. |
| 5,394,880 A | 3/1995 | Atlee, III |
| 5,396,887 A | 3/1995 | Imran |
| 5,400,778 A | 3/1995 | Jonson et al. |
| 5,400,783 A | 3/1995 | Pomeranz et al. |
| 5,411,025 A | 5/1995 | Webster, Jr. |
| 5,415,166 A | 5/1995 | Imran |
| 5,415,656 A | 5/1995 | Tihon et al. |
| 5,417,687 A | 5/1995 | Nardella et al. |
| 5,422,362 A | 6/1995 | Vincent et al. |
| 5,423,744 A | 6/1995 | Gencheff et al. |
| 5,423,811 A | 6/1995 | Imran et al. |
| 5,425,023 A | 6/1995 | Haraguchi et al. |
| 5,425,703 A | 6/1995 | Feiring |
| 5,425,811 A | 6/1995 | Mashita |
| 5,431,696 A | 7/1995 | Atlee, III |
| 5,433,730 A | 7/1995 | Alt |
| 5,437,665 A | 8/1995 | Munro |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,465,717 A | 11/1995 | Imran et al. |
| 5,471,982 A | 12/1995 | Edwards et al. |
| 5,474,530 A | 12/1995 | Passafaro et al. |
| 5,478,309 A | 12/1995 | Sweezer et al. |
| 5,496,271 A | 3/1996 | Burton et al. |
| 5,496,311 A | 3/1996 | Abele et al. |
| 5,496,312 A | 3/1996 | Klicek |

| Patent | Date | Inventor |
|---|---|---|
| 5,500,011 A | 3/1996 | Desai |
| 5,505,728 A | 4/1996 | Ellman et al. |
| 5,505,730 A | 4/1996 | Edwards |
| 5,507,791 A | 4/1996 | Sit'ko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,558,073 A | 9/1996 | Pomeranz et al. |
| 5,562,608 A | 10/1996 | Sekins et al. |
| 5,571,074 A | 11/1996 | Buckman, Jr. et al. |
| 5,571,088 A | 11/1996 | Lennox et al. |
| 5,574,059 A | 11/1996 | Regunathan et al. |
| 5,578,072 A | 11/1996 | Barone et al. |
| 5,582,609 A | 12/1996 | Swanson et al. |
| 5,588,432 A | 12/1996 | Crowley |
| 5,588,812 A | 12/1996 | Taylor et al. |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,623,940 A | 4/1997 | Daikuzono |
| 5,624,439 A | 4/1997 | Edwards et al. |
| 5,626,618 A | 5/1997 | Ward et al. |
| 5,630,425 A | 5/1997 | Panescu et al. |
| 5,630,794 A | 5/1997 | Lax et al. |
| 5,634,471 A | 6/1997 | Fairfax et al. |
| 5,641,326 A | 6/1997 | Adams |
| 5,647,870 A | 7/1997 | Kordis et al. |
| 5,660,175 A | 8/1997 | Dayal |
| 5,678,535 A | 10/1997 | DiMarco |
| 5,680,860 A | 10/1997 | Imran |
| 5,681,280 A | 10/1997 | Rusk et al. |
| 5,681,308 A | 10/1997 | Edwards et al. |
| 5,687,723 A | 11/1997 | Avitall |
| 5,688,267 A * | 11/1997 | Panescu et al. ................ 606/41 |
| 5,693,078 A | 12/1997 | Desai et al. |
| 5,694,934 A | 12/1997 | Edelman |
| 5,695,471 A | 12/1997 | Wampler |
| 5,699,799 A | 12/1997 | Xu et al. |
| 5,702,386 A * | 12/1997 | Stern et al. ..................... 606/34 |
| 5,707,218 A | 1/1998 | Maher et al. |
| 5,707,336 A | 1/1998 | Rubin |
| 5,707,352 A | 1/1998 | Sekins et al. |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,727,569 A | 3/1998 | Benetti et al. |
| 5,728,094 A | 3/1998 | Edwards |
| 5,730,128 A | 3/1998 | Pomeranz et al. |
| 5,730,704 A | 3/1998 | Avitall |
| 5,730,726 A | 3/1998 | Klingenstein |
| 5,730,741 A | 3/1998 | Horzewski et al. |
| 5,735,846 A | 4/1998 | Panescu et al. |
| 5,740,808 A | 4/1998 | Panescu et al. |
| 5,741,248 A | 4/1998 | Stern et al. |
| 5,752,518 A | 5/1998 | McGee et al. |
| 5,755,714 A | 5/1998 | Murphy-Chutorian |
| 5,755,753 A | 5/1998 | Knowlton |
| 5,759,158 A | 6/1998 | Swanson |
| 5,765,568 A | 6/1998 | Sweezer, Jr. et al. |
| 5,769,846 A | 6/1998 | Edwards et al. |
| 5,772,590 A | 6/1998 | Webster, Jr. |
| 5,779,669 A | 7/1998 | Haissaguerre et al. |
| 5,779,698 A | 7/1998 | Clayman et al. |
| 5,782,239 A | 7/1998 | Webster, Jr. |
| 5,782,797 A | 7/1998 | Schweich, Jr. et al. |
| 5,782,827 A | 7/1998 | Gough et al. |
| 5,782,848 A | 7/1998 | Lennox |
| 5,782,899 A | 7/1998 | Imran |
| 5,792,064 A | 8/1998 | Panescu et al. |
| 5,795,303 A | 8/1998 | Swanson et al. |
| 5,800,375 A | 9/1998 | Sweezer et al. |
| 5,807,306 A | 9/1998 | Shapland et al. |
| 5,810,757 A | 9/1998 | Sweezer, Jr. et al. |
| 5,810,807 A | 9/1998 | Ganz et al. |
| 5,817,028 A | 10/1998 | Anderson |
| 5,817,073 A | 10/1998 | Krespi |
| 5,820,554 A | 10/1998 | Davis et al. |
| 5,823,189 A | 10/1998 | Kordis |
| 5,827,277 A | 10/1998 | Edwards |
| 5,833,651 A | 11/1998 | Donovan et al. |
| 5,836,905 A | 11/1998 | Lemelson et al. |
| 5,836,947 A | 11/1998 | Fleischman et al. |
| 5,837,001 A | 11/1998 | Mackey |
| 5,843,075 A | 12/1998 | Taylor |
| 5,843,077 A | 12/1998 | Edwards |
| 5,846,238 A | 12/1998 | Jackson et al. |
| 5,848,969 A | 12/1998 | Panescu et al. |
| 5,848,972 A | 12/1998 | Triedman et al. |
| 5,849,026 A | 12/1998 | Zhou et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | Leveen et al. |
| 5,871,443 A | 2/1999 | Edwards et al. |
| 5,871,523 A | 2/1999 | Fleischman et al. |
| 5,873,852 A | 2/1999 | Vigil et al. |
| 5,873,865 A | 2/1999 | Horzewski et al. |
| 5,876,340 A | 3/1999 | Tu et al. |
| 5,876,399 A | 3/1999 | Chia et al. |
| 5,881,727 A | 3/1999 | Edwards |
| 5,882,346 A | 3/1999 | Pomeranz et al. |
| 5,891,135 A | 4/1999 | Jackson et al. |
| 5,891,136 A | 4/1999 | McGee et al. |
| 5,891,138 A | 4/1999 | Tu et al. |
| 5,893,847 A | 4/1999 | Kordis |
| 5,897,554 A | 4/1999 | Chia et al. |
| 5,899,882 A | 5/1999 | Waksman et al. |
| 5,904,651 A | 5/1999 | Swanson et al. |
| 5,904,711 A | 5/1999 | Flom et al. |
| 5,906,636 A | 5/1999 | Casscells, III et al. |
| 5,908,445 A | 6/1999 | Whayne et al. |
| 5,908,446 A | 6/1999 | Imran |
| 5,908,839 A | 6/1999 | Levitt et al. |
| 5,911,218 A | 6/1999 | DiMarco |
| 5,916,235 A | 6/1999 | Guglielmi |
| 5,919,147 A | 7/1999 | Jain |
| 5,919,172 A | 7/1999 | Golba, Jr. |
| 5,924,424 A | 7/1999 | Stevens et al. |
| 5,928,228 A | 7/1999 | Kordis et al. |
| 5,931,835 A | 8/1999 | Mackey |
| 5,935,079 A | 8/1999 | Swanson et al. |
| 5,941,869 A | 8/1999 | Patterson et al. |
| 5,951,494 A | 9/1999 | Wang et al. |
| 5,951,546 A | 9/1999 | Lorentzen |
| 5,954,661 A | 9/1999 | Greenspon et al. |
| 5,954,662 A | 9/1999 | Swanson et al. |
| 5,954,717 A | 9/1999 | Behl et al. |
| 5,957,961 A | 9/1999 | Maguire et al. |
| 5,964,753 A | 10/1999 | Edwards |
| 5,964,796 A | 10/1999 | Imran |
| 5,971,983 A | 10/1999 | Lesh |

| | | | | | | |
|---|---|---|---|---|---|---|
| 5,972,026 | A | 10/1999 | Laufer et al. | 6,270,476 B1 | 8/2001 | Santoianni et al. |
| 5,976,175 | A | 11/1999 | Hirano et al. | 6,273,907 B1 | 8/2001 | Laufer |
| 5,976,709 | A | 11/1999 | Kageyama et al. | 6,283,988 B1 | 9/2001 | Laufer et al. |
| 5,979,456 | A | 11/1999 | Magovern | 6,283,989 B1 | 9/2001 | Laufer et al. |
| 5,980,563 | A | 11/1999 | Tu et al. | 6,287,304 B1 | 9/2001 | Eggers et al. |
| 5,984,917 | A | 11/1999 | Fleischman et al. | 6,296,639 B1 | 10/2001 | Truckai et al. |
| 5,984,971 | A | 11/1999 | Faccioli et al. | 6,299,633 B1 | 10/2001 | Laufer |
| 5,991,650 | A | 11/1999 | Swanson et al. | 6,322,559 B1 | 11/2001 | Daulton et al. |
| 5,992,419 | A | 11/1999 | Sterzer et al. | 6,322,584 B2 | 11/2001 | Ingle et al. |
| 5,993,462 | A | 11/1999 | Pomeranz et al. | 6,338,727 B1 | 1/2002 | Noda et al. |
| 5,997,534 | A | 12/1999 | Tu et al. | 6,338,836 B1 | 1/2002 | Kuth et al. |
| 5,999,855 | A | 12/1999 | DiMarco | 6,346,104 B2 | 2/2002 | Daly et al. |
| 6,001,054 | A | 12/1999 | Regulla et al. | 6,355,031 B1 | 3/2002 | Edwards et al. |
| 6,003,517 | A | 12/1999 | Sheffield et al. | 6,379,352 B1 | 4/2002 | Reynolds et al. |
| 6,004,269 | A | 12/1999 | Crowley et al. | 6,409,723 B1 | 6/2002 | Edwards |
| 6,006,755 | A | 12/1999 | Edwards | 6,411,852 B1 | 6/2002 | Danek et al. |
| 6,008,211 | A | 12/1999 | Robinson et al. | 6,416,511 B1 | 7/2002 | Lesh et al. |
| 6,009,877 | A | 1/2000 | Edwards | 6,416,740 B1 | 7/2002 | Unger |
| 6,010,500 | A | 1/2000 | Sherman et al. | 6,423,105 B1 | 7/2002 | Iijima et al. |
| 6,014,579 | A | 1/2000 | Pomeranz et al. | 6,425,895 B1 | 7/2002 | Swanson et al. |
| 6,016,437 | A | 1/2000 | Tu et al. | 6,440,129 B1 | 8/2002 | Simpson |
| 6,023,638 | A | 2/2000 | Swanson | 6,442,435 B2 | 8/2002 | King et al. |
| 6,024,740 | A | 2/2000 | Lesh et al. | 6,458,121 B1 * | 10/2002 | Rosenstock et al. ............ 606/34 |
| 6,029,091 | A | 2/2000 | De La Rama et al. | 6,460,545 B2 | 10/2002 | Kordis |
| 6,033,397 | A | 3/2000 | Laufer et al. | 6,488,673 B1 | 12/2002 | Laufer et al. |
| 6,036,687 | A | 3/2000 | Laufer et al. | 6,488,679 B1 | 12/2002 | Swanson et al. |
| 6,036,689 | A | 3/2000 | Tu et al. | 6,493,589 B1 | 12/2002 | Medhkour et al. |
| 6,039,731 | A | 3/2000 | Taylor et al. | 6,494,880 B1 | 12/2002 | Swanson et al. |
| 6,045,549 | A | 4/2000 | Smethers et al. | 6,496,738 B2 | 12/2002 | Carr |
| 6,045,550 | A | 4/2000 | Simpson et al. | 6,514,246 B1 | 2/2003 | Swanson et al. |
| 6,050,992 | A | 4/2000 | Nichols | 6,526,320 B2 | 2/2003 | Mitchell |
| 6,053,172 | A | 4/2000 | Hovda et al. | 6,529,756 B1 | 3/2003 | Phan et al. |
| 6,053,909 | A | 4/2000 | Shadduck | 6,544,226 B1 | 4/2003 | Gaiser et al. |
| 6,056,744 | A | 5/2000 | Edwards | 6,544,262 B2 | 4/2003 | Fleischman |
| 6,056,769 | A | 5/2000 | Epstein et al. | 6,547,788 B1 | 4/2003 | Maguire et al. |
| 6,063,078 | A | 5/2000 | Wittkampf | 6,558,378 B2 | 5/2003 | Sherman et al. |
| 6,071,280 | A | 6/2000 | Edwards et al. | 6,572,612 B2 | 6/2003 | Stewart et al. |
| 6,071,281 | A * | 6/2000 | Burnside et al. ............... 606/41 | 6,575,623 B2 | 6/2003 | Werneth |
| 6,071,282 | A | 6/2000 | Fleischman | 6,575,969 B1 | 6/2003 | Rittman, III et al. |
| 6,083,255 | A | 7/2000 | Laufer et al. | 6,582,427 B1 | 6/2003 | Goble et al. |
| 6,090,104 | A | 7/2000 | Webster, Jr. | 6,582,430 B2 | 6/2003 | Hall |
| 6,092,528 | A | 7/2000 | Edwards | 6,589,235 B2 | 7/2003 | Wong et al. |
| 6,102,886 | A | 8/2000 | Lundquist et al. | 6,610,054 B1 | 8/2003 | Edwards et al. |
| 6,106,524 | A * | 8/2000 | Eggers et al. ................. 606/50 | 6,620,159 B2 | 9/2003 | Hegde |
| 6,123,702 | A | 9/2000 | Swanson et al. | 6,626,903 B2 | 9/2003 | McGuckin, Jr. et al. |
| 6,123,703 | A | 9/2000 | Tu et al. | 6,634,363 B1 | 10/2003 | Danek et al. |
| 6,139,527 | A | 10/2000 | Laufer et al. | 6,635,056 B2 | 10/2003 | Kadhiresan et al. |
| 6,139,571 | A | 10/2000 | Fuller et al. | 6,638,273 B1 | 10/2003 | Farley et al. |
| 6,142,993 | A | 11/2000 | Whayne et al. | 6,640,120 B1 | 10/2003 | Swanson et al. |
| 6,143,013 | A | 11/2000 | Samson et al. | 6,645,200 B1 | 11/2003 | Koblish et al. |
| 6,149,647 | A | 11/2000 | Tu et al. | 6,652,548 B2 | 11/2003 | Evans et al. |
| 6,152,143 | A | 11/2000 | Edwards | 6,669,693 B2 | 12/2003 | Friedman |
| 6,152,899 | A | 11/2000 | Farley et al. | 6,673,068 B1 | 1/2004 | Berube |
| 6,159,194 | A | 12/2000 | Eggers et al. | 6,692,492 B2 | 2/2004 | Simpson et al. |
| 6,179,833 | B1 | 1/2001 | Taylor | 6,699,243 B2 | 3/2004 | West et al. |
| 6,183,468 | B1 | 2/2001 | Swanson et al. | 6,714,822 B2 | 3/2004 | King et al. |
| 6,198,970 | B1 | 3/2001 | Freed et al. | 6,723,091 B2 | 4/2004 | Goble et al. |
| 6,200,311 | B1 | 3/2001 | Danek et al. | 6,743,197 B1 | 6/2004 | Edwards |
| 6,200,332 | B1 | 3/2001 | Del Giglio | 6,749,604 B1 | 6/2004 | Eggers et al. |
| 6,200,333 | B1 | 3/2001 | Laufer | 6,749,606 B2 | 6/2004 | Keast et al. |
| 6,210,367 | B1 | 4/2001 | Carr | 6,767,347 B2 | 7/2004 | Sharkey et al. |
| 6,212,433 | B1 | 4/2001 | Behl | 6,770,070 B1 | 8/2004 | Balbierz |
| 6,214,002 | B1 | 4/2001 | Fleischman et al. | 6,802,843 B2 | 10/2004 | Truckai et al. |
| 6,216,043 | B1 | 4/2001 | Swanson et al. | 6,805,131 B2 | 10/2004 | Kordis |
| 6,216,044 | B1 | 4/2001 | Kordis | 6,837,888 B2 | 1/2005 | Ciarrocca et al. |
| 6,217,576 | B1 | 4/2001 | Tu et al. | 6,840,243 B2 | 1/2005 | Deem et al. |
| 6,235,024 | B1 | 5/2001 | Tu | 6,849,073 B2 | 2/2005 | Hoey et al. |
| 6,241,727 | B1 | 6/2001 | Tu et al. | 6,852,091 B2 | 2/2005 | Edwards et al. |
| 6,245,065 | B1 | 6/2001 | Panescu et al. | 6,852,110 B2 | 2/2005 | Roy et al. |
| 6,254,598 | B1 | 7/2001 | Edwards et al. | 6,866,662 B2 | 3/2005 | Fuimaono et al. |
| 6,258,087 | B1 | 7/2001 | Edwards et al. | 6,881,213 B2 | 4/2005 | Ryan et al. |
| 6,264,653 | B1 | 7/2001 | Falwell | 6,893,436 B2 | 5/2005 | Woodard et al. |
| 6,269,813 | B1 | 8/2001 | Fitzgerald et al. | 6,893,439 B2 | 5/2005 | Fleischman |

| | | |
|---|---|---|
| 6,895,267 B2 | 5/2005 | Panescu et al. |
| 6,904,303 B2 | 6/2005 | Phan et al. |
| 6,917,834 B2 | 7/2005 | Koblish et al. |
| 6,939,346 B2 | 9/2005 | Kannenberg et al. |
| 6,954,977 B2 | 10/2005 | Maguire et al. |
| 7,027,869 B2 | 4/2006 | Danek et al. |
| 7,043,307 B1 | 5/2006 | Zelickson et al. |
| 7,104,987 B2 | 9/2006 | Biggs et al. |
| 7,104,990 B2 | 9/2006 | Jenkins et al. |
| 7,118,568 B2 | 10/2006 | Hassett et al. |
| 7,122,033 B2 | 10/2006 | Wood |
| 7,131,445 B2 | 11/2006 | Amoah |
| 7,186,251 B2 | 3/2007 | Malecki et al. |
| 7,198,635 B2 | 4/2007 | Danek et al. |
| 7,200,445 B1 | 4/2007 | Dalbec et al. |
| 7,241,295 B2 | 7/2007 | Maguire |
| 7,255,693 B1 | 8/2007 | Johnston et al. |
| 7,264,002 B2 | 9/2007 | Danek et al. |
| 7,266,414 B2 | 9/2007 | Cornelius et al. |
| 7,273,055 B2 | 9/2007 | Danek et al. |
| 7,425,212 B1 | 9/2008 | Danek et al. |
| 7,542,802 B2 | 6/2009 | Biggs et al. |
| 7,556,624 B2 | 7/2009 | Laufer et al. |
| 7,740,017 B2 | 6/2010 | Danek et al. |
| 2003/0050631 A1 | 3/2003 | Mody et al. |
| 2003/0065371 A1 | 4/2003 | Satake |
| 2003/0069570 A1 | 4/2003 | Witzel et al. |
| 2003/0187430 A1 | 10/2003 | Vorisek |
| 2003/0236455 A1 | 12/2003 | Swanson et al. |
| 2004/0010289 A1 | 1/2004 | Biggs et al. |
| 2004/0153056 A1 | 8/2004 | Muller et al. |
| 2004/0249401 A1 | 12/2004 | Rabiner et al. |
| 2005/0010270 A1 | 1/2005 | Laufer |
| 2005/0096644 A1 | 5/2005 | Hall et al. |
| 2005/0171396 A1 | 8/2005 | Pankratov et al. |
| 2005/0193279 A1 | 9/2005 | Daners |
| 2005/0203503 A1 | 9/2005 | Edwards et al. |
| 2005/0240176 A1 | 10/2005 | Oral et al. |
| 2005/0251128 A1 | 11/2005 | Amoah |
| 2006/0062808 A1 | 3/2006 | Laufer et al. |
| 2006/0079887 A1 | 4/2006 | Buysse et al. |
| 2006/0089637 A1 | 4/2006 | Werneth et al. |
| 2006/0135953 A1 | 6/2006 | Kania et al. |
| 2006/0137698 A1 | 6/2006 | Danek et al. |
| 2006/0247617 A1 | 11/2006 | Danek et al. |
| 2006/0247618 A1 | 11/2006 | Kaplan et al. |
| 2006/0247619 A1 | 11/2006 | Kaplan et al. |
| 2006/0247726 A1 | 11/2006 | Biggs et al. |
| 2006/0247746 A1 | 11/2006 | Danek et al. |
| 2006/0254600 A1 | 11/2006 | Danek et al. |
| 2006/0278243 A1 | 12/2006 | Danek et al. |
| 2006/0278244 A1 | 12/2006 | Danek et al. |
| 2006/0282071 A1 | 12/2006 | Utley et al. |
| 2007/0074719 A1 | 4/2007 | Danek et al. |
| 2007/0083194 A1 | 4/2007 | Kunis et al. |
| 2007/0083197 A1 | 4/2007 | Danek et al. |
| 2007/0100390 A1 | 5/2007 | Danaek et al. |
| 2007/0102011 A1 | 5/2007 | Danek et al. |
| 2007/0106292 A1 | 5/2007 | Kaplan et al. |
| 2007/0106296 A1 | 5/2007 | Laufer et al. |
| 2007/0106348 A1 | 5/2007 | Laufer |
| 2007/0118184 A1 | 5/2007 | Danek et al. |
| 2007/0118190 A1 | 5/2007 | Danek |
| 2007/0123958 A1 | 5/2007 | Laufer |
| 2007/0123961 A1 | 5/2007 | Danek et al. |
| 2007/0129720 A1 | 6/2007 | Demarais et al. |
| 2008/0004596 A1 | 1/2008 | Yun et al. |
| 2008/0097424 A1 | 4/2008 | Wizeman et al. |
| 2008/0255642 A1 | 10/2008 | Zarins et al. |
| 2009/0018538 A1 | 1/2009 | Webster et al. |
| 2009/0030477 A1 | 1/2009 | Jarrard |
| 2009/0043301 A1 | 2/2009 | Jarrard et al. |
| 2009/0069797 A1 | 3/2009 | Danek et al. |
| 2009/0112203 A1 | 4/2009 | Danek et al. |
| 2009/0143705 A1 | 6/2009 | Danek et al. |
| 2009/0143776 A1 | 6/2009 | Danek et al. |
| 2009/0192505 A1 | 7/2009 | Askew et al. |
| 2009/0192508 A1 | 7/2009 | Laufer et al. |
| 2009/0306644 A1 | 12/2009 | Mayse et al. |

FOREIGN PATENT DOCUMENTS

| | | |
|---|---|---|
| EP | 189329 A3 | 6/1987 |
| EP | 286145 A2 | 10/1988 |
| EP | 280225 A3 | 3/1989 |
| EP | 286145 A3 | 10/1990 |
| EP | 282225 B1 | 6/1992 |
| EP | 0 908 713 A1 | 4/1999 |
| EP | 908150 A1 | 4/1999 |
| EP | 768091 B1 | 7/2003 |
| EP | 1297795 B1 | 8/2005 |
| FR | 2659240 B1 | 7/1997 |
| GB | 2233293 A | 1/1991 |
| GB | 2233293 | 2/1994 |
| JP | 59167707 A2 | 9/1984 |
| JP | 7289557 A2 | 11/1995 |
| JP | 9047518 A2 | 2/1997 |
| JP | 9243837 A2 | 9/1997 |
| JP | 10026709 A2 | 1/1998 |
| RU | 2053814 C1 | 2/1996 |
| RU | 2091054 C1 | 9/1997 |
| SU | 545358 T | 2/1977 |
| WO | WO-8911311 A1 | 11/1989 |
| WO | WO-9502370 A3 | 1/1995 |
| WO | WO-9510322 A1 | 4/1995 |
| WO | WO-9604860 A1 | 2/1996 |
| WO | WO-9610961 A1 | 4/1996 |
| WO | WO-9732532 A1 | 9/1997 |
| WO | WO-9733715 A1 | 9/1997 |
| WO | WO-9737715 A1 | 10/1997 |
| WO | WO-9740751 A1 | 11/1997 |
| WO | WO-9844854 A1 | 10/1998 |
| WO | WO-9852480 A1 | 11/1998 |
| WO | WO-9856234 A1 | 12/1998 |
| WO | WO-9856324 A1 | 12/1998 |
| WO | WO-9858681 A2 | 12/1998 |
| WO | WO 99/03413 A1 | 1/1999 |
| WO | WO-9913779 A2 | 3/1999 |
| WO | WO-9932040 A1 | 7/1999 |
| WO | WO-9934741 A1 | 7/1999 |
| WO | WO-9944506 A1 | 9/1999 |
| WO | WO-9945855 A1 | 9/1999 |
| WO | WO-9964109 A1 | 12/1999 |
| WO | WO-0051510 A1 | 9/2000 |
| WO | WO-0062699 A3 | 10/2000 |
| WO | WO-0103642 A1 | 1/2001 |
| WO | WO-0232333 A1 | 4/2002 |
| WO | WO-0232334 A1 | 4/2002 |
| WO | WO-2009082433 A2 | 7/2009 |
| WO | WO-2009137819 A1 | 11/2009 |

OTHER PUBLICATIONS

Bel, et al., ""Hot stuff": bronchial thermoplasty for asthma," American Journal of Respiratory and Critical Care Medicine, 2006, 173, 941-943.

Brown R. H., et al., "Effect of bronchial thermoplasty on airway distensibility," European Respiratory Journal, 2005, 26 (2), 277-282.

Brown R. H., et al., "In vivo evaluation of the effectiveness of bronchial thermoplasty with computed tomography," Journal of Applied Physiology, 2005, 98, 1603-1606.

Chhajed P., et al., "Will there be a role for bronchoscopic radiofrequency ablation?," J Bronchol, 2005, 12 (3), 184-186.

Co-pending U.S. Appl. No. 09/095,323 filed Jun. 10, 1998, Inventor Laufer et al.

Co-pending U.S. Appl. No. 09/244,173, filed Feb. 4, 1999, Inventor Laufer et al.

Co-pending U.S. Appl. No. 12/640,644, filed Dec. 17, 2009, Inventor Jerry Jarrard.
Co-pending U.S. Appl. No. 12/727,156, filed Mar. 18, 2010, Inventor Danek et al.
Co-pending U.S. Appl. No. 12/765,704, filed Apr. 22, 2010 Inventor Danek et al.
Cox G., et al., "Asthma Control during the Year after Bronchial Thermoplasty," The New England journal of medicine, 2007, 356 (13), 1327-1337.
Cox G., et al., "Bronchial Thermoplasty for Asthma," American Journal of Respiratory and Critical Care Medicine, 2006, 173, 965-969.
Cox G., et al., "Bronchial Thermoplasty: Long-Term Follow-Up and Patient Satisfaction," Chest, 2004, 126 (4), 822s.
Cox G., et al., "Bronchial Thermoplasty: One-Year Update, American Thoracic Society Annual Meeting," Am J Respir Crit Care Med, 2004, 169, A313.
Cox G., et al., "Clinical Experience With Bronchial Thermoplasty for the Treatment of Asthma," Chest, 2003, 124, 106S.
Cox G., et al., "Development of a Novel Bronchoscopic Therapy for Asthma," Journal of Allergy and Clinical Immunology, 2003, 113 (2), S33.
Cox G., et al., "Early Clinical Experience with Bronchial Thermoplasty for the Treatment of Asthma, American Thoracic Society Annual Meeting," 2002, 1068.
Cox G., et al., "Impact of bronchial thermoplasty on asthma status: interim results from the AIR trial.European Respiratory Society Annual Meeting. Munich, Germany," 2006, 1 page.
Cox G., et al., "Radiofrequency ablation of airway smooth muscle for sustained treatment of asthma: preliminary investigations," European Respiratory Journal, 2004, 24, 659-663.
Danek C. J., et al., "Asthma Intervention Research (AIR) Trial Evaluating Bronchial Thermoplasty™: Early Results, American Thoracic Society Annual Meeting," 2002, 1 page.
Danek C. J., et al., "Bronchial thermoplasty reduces canine airway responsiveness to local methacholine challenge, American Thoracic Society Annual Meeting," 2002, 1 page.
Danek C. J., et al., "Reduction in airway hyperresponsiveness to methacholine by the application of RF energy in dogs," J Appl Physiol, 2004, 97, 1946-1953.
Dierkesmann, et al., "Indication and Results of Endobronchial Laser Therapy," Lung, 1990, 168, 1095-1102.
Erle C. H., et al., "Botulinum toxin: a novel therapeutic option for bronchial asthma?," Medical Hypotheses, 2006, 66, 915-919.
Hogg J. C., "The Pathology of Asthma," APMIS, 1997, 105 (10), 735-745.
Ivanyuta O. M., et al., "Effect of Low-Power Laser Irradiation of Bronchial Mucosa on the State of Systemic and Local Immunity in Patients with Chronic Bronchitis," Problemy Tuberkuleza, 1991, 6, 26-29.
James, et al., "The Mechanics of Airway Narrowing in Asthma," Am. Rev. Respir. Dis., 1989, 139, 242-246.
Johnson S. R., et al., "Synthetic Functions of Airway Smooth Muscle in Asthma," Trends Pharmacol. Sci., 1997, 18 (8), 288-292.
Julian Solway M. D., et al., "Airway Smooth Muscle as a Target for Asthma Therapy," The New England journal of medicine, 2007, 356 (13), 1367-1369.
Kitamura S., "Color Atlas of Clinical Application of Fiberoptic Bronchoscopy," 1990, Year Book Medical Publishers, 17.
Laviolette, et al., "Asthma Intervention Research (Air) Trial: Early Safety Assessment of Bronchial Thermoplasty," Am J Respir Crit Care Med, 2004, 169, A314.
Leff, et al., "Bronchial Thermoplasty Alters Airway Smooth Muscle and Reduces Responsiveness in Dogs: A Possible Procedure for the Treatment of Asthma, American Thoracic Society Annual Meeting," 2002, 1 page.
Lombard, et al., "Histologic Effects of Bronchial Thermoplasty of Canine and Human Airways, American Thoracic Society Annual Meeting," 2002, 1 page.

Macklem P. T., "Mechanical Factors Determining Maximum Bronchoconstriction," European Respiratory Journal, 1989, 6, 516s-519s.
Mayse M. L., et al., "Clinical Pearls for Bronchial Thermoplasty," J Bronchol, 2007, 14 (2), 115-123.
Miller J. D., et al., "A Prospective Feasibility Study of Bronchial Thermoplasty in the Human Airway," 2005, 127, 1999-2006.
Miller J. D., et al., "Bronchial Thermoplasty Is Well Tolerated by Non-Asthmatic Patients Requiring Lobectomy, American Thoracic Society Annual Meeting," 2002, 1 page.
Netter F. H., "Respiratory System: A Compilation of Paintings Depicting Anatomy and Embryology, Physiology, Pathology, Pathophysiology, and Clinical Features and Treatment of Diseases,In the CIBA Collection of Medical Illustrations M.B. Divertie, ed., Summit: New Jerse," 1979, 7, 119-135.
Notice of final Rejection, Japanese Patent Application No. 2000-553172, dated Sep. 2, 2008, 5 pages.
PCT International search report for application No. PCT/US00/05412 mailed on Jun. 20, 2000, 2 pages.
PCT International search report for application No. PCT/US00/18197 mailed on Oct. 3, 2000, 1 page.
PCT International search report for application No. PCT/US00/28745 mailed on Mar. 28, 2001, 6 pages.
PCT International search report for application No. PCT/US01/32321 mailed on Jan. 18, 2002, 2 pages.
PCT International search report for application No. PCT/US98/03759 mailed on Jul. 30, 1998, 1 page.
PCT International search report for application No. PCT/US98/26227 mailed on Mar. 25, 1999, 1 page.
PCT International search report for application No. PCT/US99/00232 mailed on Mar. 4, 1999, 1 page.
PCT International search report for application No. PCT/US99/12986 mailed on Sep. 29, 1999, 1 page.
Provotorov, et al., "The Clinical Efficacy of Treating Patients with Nonspecific Lung Disease by Using Low-energy Laser Irradiation and Intrapulmonary Drug Administration, ISSN: 0040-3660," Terapevticheskii Arkhiv (USSR), 1991, 62 (12), 18-23.
Rubin, et al., "Bronchial thermoplasty improves asthma status of moderate to severe perisstent asthmatics over and above current standard-of-care, American College of Chest Physicians," 2006, 2 pages.
Shesterina M. V., et al., "Effect of laser therapy on immunity in patients with bronchial asthma and pulmonary tuberculosis," 1993, 23-26.
Sterk P. J., et al., "Heterogeneity of airway hyperresponsiveness: time for unconventional, but traditional, studies," J Appl Physiol, 2004, 96, 2017-2018.
Toma, et al., "Brave new world for interventional bronchoscopy," Thorax, 2005, 60, 180-181.
Trow T., "Clinical Year in Review I Diagnostic Imaging, Asthma, Lung Transplantation, and Interventional Pulmonology," Proceedings of the American Thoracic Society, 2006, 3, 553-556.
Vorotnev, et al., "Low energy laser treatment of chronic obstructive bronchitis in a general rehabilitation center,ISSN: 0040-3660," Terapevticheskii Arkhiv, 1997, 69 (3), 17-19.
Wayne Mitzner, "Airway Smooth Muscle The appendix of the Lung," American Journal of Respiratory and Critical Care Medicine, 2004, 169, 787-790.
Wiggs B. R., et al., "On the Mechanism of Mucosal Folding in Normal and Asthmatic Airways," J. Appl. Physiol., 1997, 83 (6), 1814-1821.
Wilson S. R., et al., "Global assessment after bronchial thermoplasty: the patients perspective," Journal of Outcomes Research, 2006, 10, 37-46.
Wizeman, et al., "A Computer Model of Thermal Treatment of Airways by Radiofrequency (RF) Energy Delivery, American Thoracic Society Annual Meeting," 2007, 1 page.

* cited by examiner

CONTROL SYSTEM AND PROCESS FOR APPLICATION OF ENERGY TO AIRWAY WALLS AND OTHER MEDIUMS

CROSS REFERENCE TO RELATED APPLICATIONS

This application is a divisional of U.S. patent application Ser. No. 10/414,411 filed Apr. 14, 2003, now U.S. Pat. No. 7,104,987, which is a continuation of International Patent Application No. PCT/US01/32321 filed Oct. 17, 2001 and is a continuation-in-part of International Patent Application No. PCT/US00/28745 filed Oct. 17, 2000, the contents of which are hereby incorporated in their entirety.

FIELD OF THE INVENTION

This invention is related to systems for applying energy to lung airways and in particular, to a system and method for controlling the energy delivered to the airways using a PID algorithm to minimize error between a preset temperature and a measured temperature.

BACKGROUND

Various obstructive airway diseases have some reversible component. Examples include COPD and asthma. There are an estimated 10 million Americans afflicted with Asthma. Asthma is a disease in which bronchoconstriction, excessive mucus production, and inflammation and swelling of airways occur, causing widespread but variable airflow obstruction thereby making it difficult for the asthma sufferer to breathe. Asthma is a chronic disorder, primarily characterized by persistent airway inflammation. Asthma is further characterized by acute episodes of additional airway narrowing via contraction of hyper-responsive airway smooth muscle.

Reversible aspects of obstructive pulmonary disease generally include excessive mucus production in the bronchial tree. Usually, there is a general increase in bulk (hypertrophy) of the large bronchi and chronic inflammatory changes in the small airways. Excessive amounts of mucus are found in the airways and semisolid plugs of mucus may occlude some small bronchi. Also, the small airways are narrowed and show inflammatory changes. Reversible aspects include partial airway occlusion by excess secretions and airway narrowing secondary to smooth muscle contraction, bronchial wall edema and inflammation of the airways.

In asthma, chronic inflammatory processes in the airway play a central role in increasing the resistance to airflow within the lungs. Many cells and cellular elements are involved in the inflammatory process, particularly mast cells, eosinophils T lymphocytes, neutrophils, epithelial cells, and even airway smooth muscle itself. The reactions of these cells result in an associated increase in the existing sensitivity and hyper-responsiveness of the airway smooth muscle cells that line the airways to the particular stimuli involved.

The chronic nature of asthma can also lead to remodeling of the airway wall (i.e., structural changes such as thickening or edema) which can further affect the function of the airway wall and influence airway hyper-responsiveness. Other physiologic changes associated with asthma include excess mucus production, and if the asthma is severe, mucus plugging, as well as ongoing epithelial denudation and repair. Epithelial denudation exposes the underlying tissue to substances that would not normally come in contact with them, further reinforcing the cycle of cellular damage and inflammatory response.

In susceptible individuals, asthma symptoms include recurrent episodes of shortness of breath (dyspnea), wheezing, chest tightness, and cough. Currently, asthma is managed by a combination of stimulus avoidance and pharmacology.

Stimulus avoidance is accomplished via systematic identification and minimization of contact with each type of stimuli. It may, however, be impractical and not always helpful to avoid all potential stimuli.

Pharmacological management of asthma includes: (1) long term control through use of anti-inflammatories and long-acting bronchodilators and (2) short term management of acute exacerbations through use of short-acting bronchodilators. Both of these approaches require repeated and regular use of the prescribed drugs. High doses of corticosteroid anti-inflammatory drugs can have serious side effects that require careful management. In addition, some patients are resistant to steroid treatment. The difficulty involved in patient compliance with pharmacologic management and the difficulty of avoiding stimulus that triggers asthma are common barriers to successful asthma management. Current management techniques are thus neither completely successful nor free from side effects. Accordingly, it would be desirable to provide a system and method which improves airflow without the need for patient compliance.

Various energy delivering systems have been developed to intraluminally treat anatomical structures and lumen other than the lung airways. Unfortunately, the systems which are useful in treating such structures are generally not helpful in developing techniques to treat the lung airways because the lung airways are markedly different than other tissue structures. For example, lung airways are particularly heterogeneous. Variations in lung tissue structure occur for a number of reasons such as: the branching pattern of the tracheobronchial tree leads to local variation in the size and presence of airways; the vasculature of the lungs is a similar distributed network causing variation in size and presence of blood vessels; within the airways are variable amounts of differing structures such as cartilage, airway smooth muscle, and mucus glands and ducts; and energy delivery may also be influenced differently at the periphery, near the outer surface of a lung lobe, than in the central portion.

Lung airways also include a number of protruding folds. Other tissue structures such as blood vessels typically do not have the folds found in airways. Airways contain mucous and air whereas other structures contain different substances. The tissue chemistry between various lumens and airways is also different. In view of these differences, it is not surprising that conventional energy delivering systems cannot be universally applied to treat all tissue structures. Moreover, power shut-offs and other safety mechanisms must be precisely tailored to specific tissue so that the tissue is not harmed by application of excess energy.

Accordingly, an intraluminal RF energy delivering system that is capable of safely delivering RF energy to lung airways is desired. In particular, a system which is capable of controlling the temperature when treating an airway of an asthma or COPD patient is desired. It is also desirable to provide a system having built-in safeguards that shut the power off thereby preventing damage to the subject tissue or collateral tissue.

SUMMARY OF THE INVENTION

The present invention includes a system for delivering energy to an airway wall of a lung comprising an energy delivering apparatus and a PID controller. The energy delivering apparatus may include a flexible elongated member and a distal expandable basket having at least one electrode for transferring energy to the airway wall and at least one temperature sensor for measuring temperature ($T_M$) of the airway wall when energy is delivered to the airway wall. The system further comprises a PID controller for determining a new power set point ($P_{i+1}$) based on an error (e) between a preset temperature ($T_S$) and the measured temperature wherein the PID controller applies an algorithm having a variable gain factor (G).

In one variation of the present invention, the algorithm is $P_{i+1}=P_i+G(\alpha e_i+\beta e_{i-1}+\gamma e_{i-2})$ where $\alpha$, $\beta$ and $\gamma$ are preset values. For instance, in one variation of the present invention, $\alpha$ is from 1 to 2; $\beta$ is from −1 to −2; and $\gamma$ is from −0.5 to 0.5. In another variation of the present invention, $\alpha$, $\beta$, $\gamma$ are 1.6, −1.6, and 0.0 respectively.

In another variation of the present invention, the gain factor used in the PID algorithm is reset 0.1 to 2 seconds after energy delivery has begun. The gain factor can also be reset 0.5 seconds after energy delivery has begun. The invention includes resetting G to 0.9 to 1.0 if a temperature rise in ° C. per Joule is less than or equal to 2.5; 0.4 to 0.5 if a temperature rise in ° C. per Joule is between 2.5 to 5.0; to 0.2 to 0.3 if a temperature rise in ° C. per Joule is equal to 5.0 to 7.5; and to 0.1 to 0.2 if a temperature rise in ° C. per Joule is greater than 7.5. Initially, the gain factor is equal to 0.4 to 0.5 and preferably 0.45 to 0.47.

In another variation of the present invention, the PID algorithm is $P_{i+1}=P_i+(G_1 e_i+G_2 e_{i-1}+G_3 e_{i-2})$ and $G_1$, $G_2$ and $G_3$ are variable gain factors. The invention includes configuring the controller such that $G_1$, $G_2$ and $G_3$ are reset to 0.9 to 2.00, −0.9 to −2.00 and 0.5 to −0.5 respectively if a temperature rise in ° C. per Joule is less than or equal to 2.5; to 0.40 to 1.00, −0.40 to −1.00 and 0.25 to −0.25 respectively if a temperature rise in ° C. per Joule is between 2.5 to 5.0; to 0.20 to 0.60, −0.20 to −0.60 and 0.15 to −0.15 respectively if a temperature rise in ° C. per Joule is equal to 5.0 to 7.5; and to 0.10 to 0.40, −0.10 to −0.40 and 0.10 to −0.10 respectively if a temperature rise in ° C. per Joule is greater than 7.5. Each of the variable gain factors may be equal to a product of at least one preset value and at least one variable value.

In another variation of the present invention, the controller is configured such that the energy delivery is terminated if the energy delivered exceeds a maximum energy such as 120 joules.

In another variation of the present invention, the controller is configured to deliver energy for an activation time period such as up to 15 seconds, 8 to 12 seconds, or 10 seconds.

In another variation of the present invention, the controller is configured such that $T_S$ is set at a value between 60 to 80° C., or 65° C.

In another variation of the present invention, the controller is configured to measure impedance and said energy delivery is terminated when said impedance drops below a preset impedance value such as 40 to 60 ohms.

In another variation of the present invention, the controller is configured to terminate the energy delivery if $T_M$ exceeds $T_S$ by a pre-selected value such as 10, 15 or 20° C.

In another variation of the present invention, the controller is configured to terminate the energy delivery if the output power is greater or equal to a nominal output power and $T_M$ drops by a critical temperature difference within a sampling period. The invention includes a nominal output power set at a value of at least 17 watts; the sampling period is set at a value of at least 0.5 seconds; and the critical temperature difference is 2° C.

In another variation of the present invention, the controller is configured to terminate the energy delivery if said $T_M$ averaged over a time window exceeds $T_S$ by a fixed temperature difference. The fixed temperature difference may be a value between 1 and 10° C. or 5° C. The time window is between 1 and 5 seconds or 2 seconds.

In another variation of the present invention, the controller is configured to terminate if the measured temperature drops by 10 or more ° C. in a sample period such as 1.0 seconds or 0.2 seconds.

Another variation of the present invention is a method for treating a lung by transferring energy from an active region of an energy delivery apparatus to an airway wall of the lung. The energy delivery apparatus includes a flexible elongate body and a distal section and the active region is located in the distal section. The energy delivery apparatus further has a temperature sensor located in the distal section for measuring a temperature ($T_M$) of said airway wall and the method comprises the following steps: setting a preset temperature ($T_S$); determining a power set point ($P_i$) to deliver energy from the active region to the target medium; measuring the $T_M$ using the temperature sensor; and determining a new power set point ($P_{i+1}$) based on an error (e) between the preset temperature ($T_S$) and the measured temperature ($T_M$) using a PID algorithm.

In yet another variation of the present invention, a process for transferring energy to a target medium using an energy delivery apparatus is provided. The energy delivery apparatus includes a flexible elongate body and a distal section wherein the distal section includes an expandable basket with at least one active region for transferring energy to the target medium. The energy delivery apparatus further has a temperature sensor located in the distal section for measuring a temperature ($T_M$) of the target medium. The process comprises the following steps: setting a preset temperature ($T_S$); determining a power set point ($P_i$) to deliver energy from the active region to the target medium; measuring $T_M$ using the temperature sensor; and determining a new power set point ($P_{i+1}$) based on an error (e) between the preset temperature ($T_S$) and the measured temperature ($T_M$) using an algorithm having a variable gain factor. The energy may be delivered to an airway wall of a lung in vivo, in vitro or to another target such as a sponge or towel which may be moistened with saline solution. Saline solution increases the conductivity of the target.

In one variation of the present invention, the algorithm is $P_{i+1}=P_i+G(\alpha e_i+\beta e_{i-1}+\gamma e_{i-2})$ where $\alpha$, $\beta$ and $\gamma$ are preset values: $\alpha$ is from 1 to 2; $\beta$ is from −1 to −2; and $\gamma$ is from −0.5 to 0.5. In another variation of the present invention, $\alpha$, $\beta$, $\gamma$ are 1.6, −1.6, and 0.0 respectively.

In another variation of the present invention, the gain factor is reset 0.1 to 2 seconds after energy delivery has begun. The gain factor can also be reset 0.5 seconds after energy delivery has begun. The invention includes resetting G to 0.9 to 1.0 if a temperature rise in ° C. per Joule is less than or equal to 2.5; 0.4 to 0.5 if a temperature rise in ° C. per Joule is between 2.5 to 5.0; to 0.2 to 0.3 if a temperature rise in ° C. per Joule is equal to 5.0 to 7.5; and to 0.1 to 0.2 if a temperature rise in ° C. per Joule is greater than 7.5. Initially, the gain factor is equal to 0.4 to 0.5 and preferably 0.45 to 0.47.

In another variation of the present invention, the energy delivery is terminated if the energy delivered exceeds a maximum energy such as 120 joules.

In another variation of the present invention, energy is delivered for an activation time period such as 0 to 15 seconds, 8 to 12 seconds, or 10 seconds.

In another variation of the present invention, $T_S$ is set at a value between 60 to 80, or 65° C.

In another variation of the present invention, impedance is measured and energy delivery is terminated when the impedance drops below a preset impedance value such as 40 to 60 ohms.

In another variation of the present invention, the energy is terminated if $T_M$ exceeds $T_S$ by a pre-selected value such as 10, 15 or 20° C.

In another variation of the present invention, energy is terminated if the output power is greater or equal to a nominal output power and $T_M$ drops by a critical temperature difference within a sampling period. In variations of the present invention, the nominal output power is set at a value of at least 17 watts; the sampling period is set at a value of at least 0.5 seconds; and the critical temperature difference is 2° C.

In another variation, the energy delivery apparatus is configured to deliver an amount of power up to a maximum power. The maximum power can be from 10 to 40 watts and preferably from 15 to 20 watts.

In another variation of the present invention, energy delivery is terminated if $T_M$ averaged over a time window exceeds $T_S$ by a fixed temperature difference. The fixed temperature difference may be a value between 1 and 10° C. or 5° C. The time window is between 1 and 5 seconds or 2 seconds.

In another variation of the present invention, the energy delivery is terminated if the measured temperature drops by 10 or more ° C. in a sample period such as 1.0 seconds or 0.2 seconds.

BRIEF DESCRIPTION OF THE DRAWINGS

The invention will now be described in greater detail with reference to the various embodiments illustrated in the accompanying drawings.

DETAILED DESCRIPTION

Figure 1:
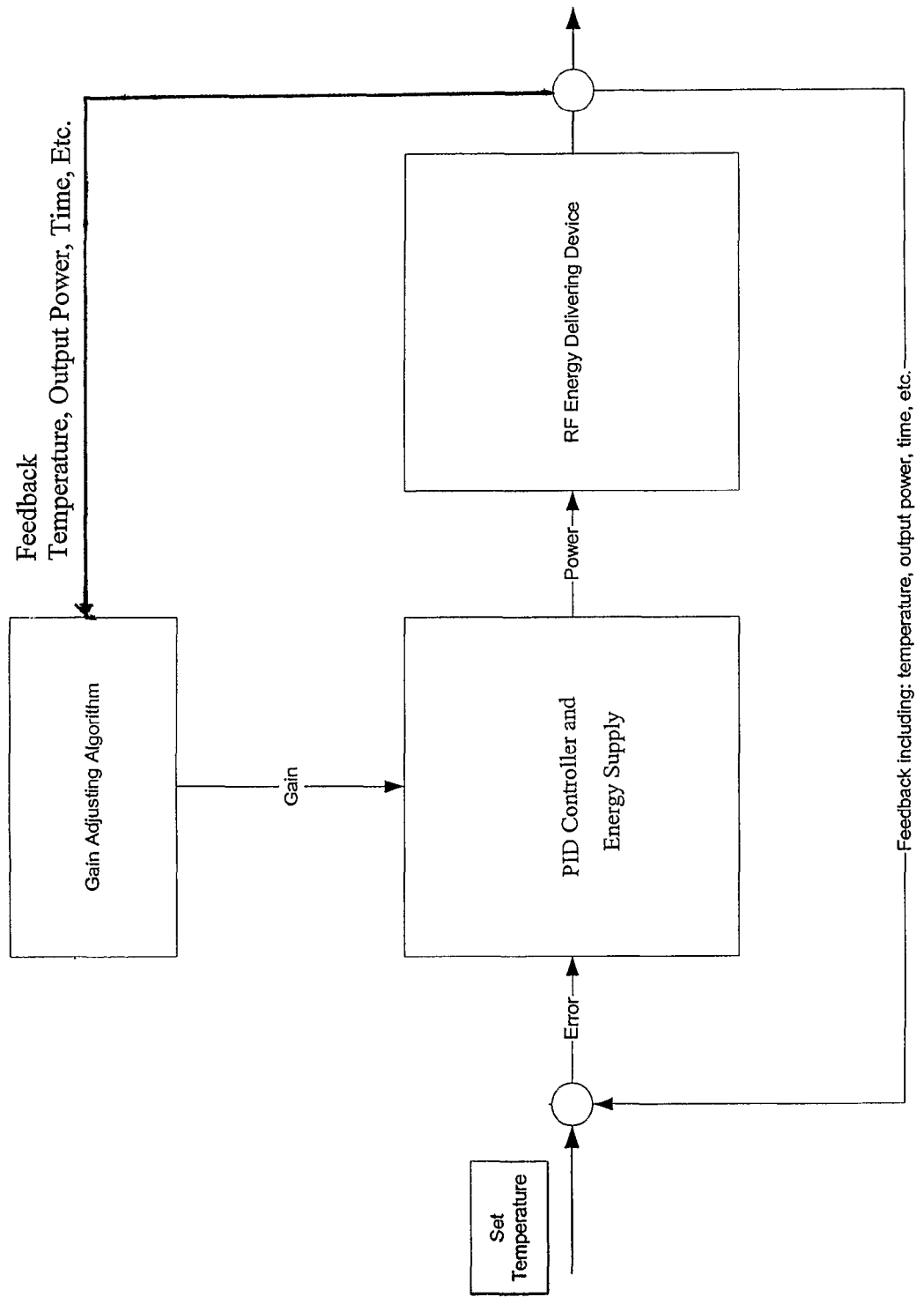
FIG. 1 is a block diagram of a feedback loop of the present invention.

The present invention includes a controller and an energy deliver apparatus to deliver energy to the airway walls of the lungs. Amongst other features, the controller includes a feedback loop having a variable gain factor as diagramed in FIG. 1. The system is useful in treating asthma and various symptoms of reversible obstructive pulmonary disease. Examples of suitable applications and methods are disclosed in International Application No. PCT/US00/28745 filed Oct. 17, 2000.

Figure 2A:
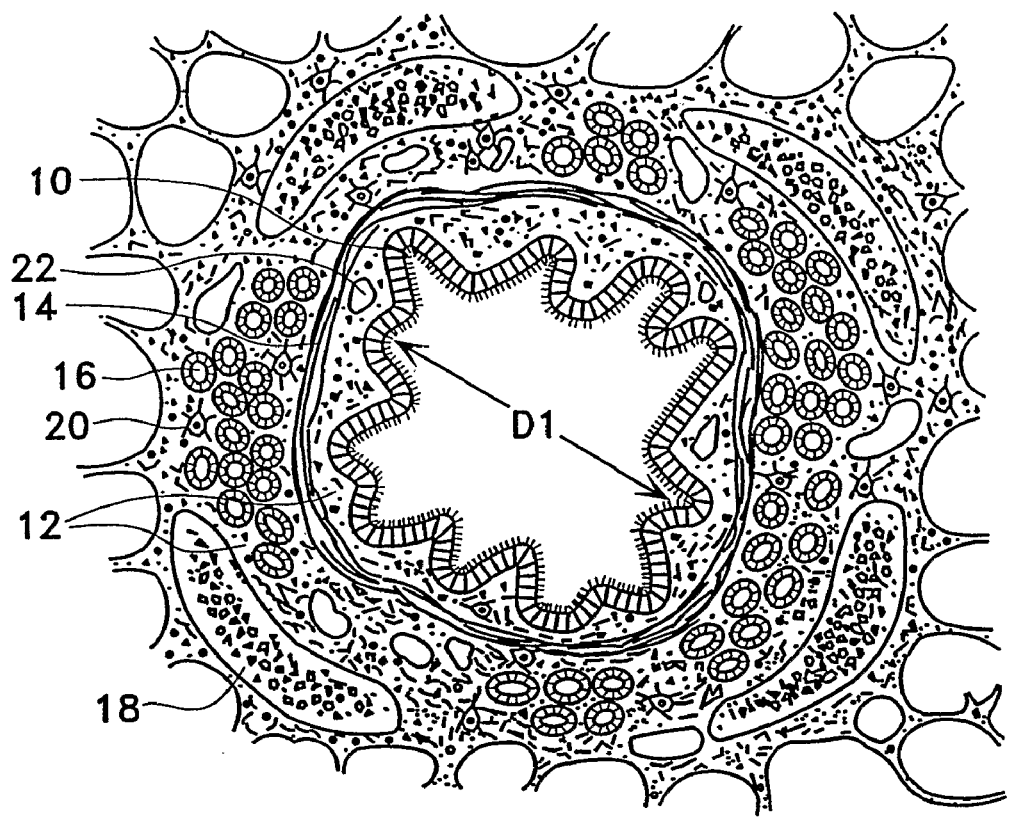
FIG. 2A is a cross sectional view of a medium sized bronchus in a healthy patient.
Figure 2B:
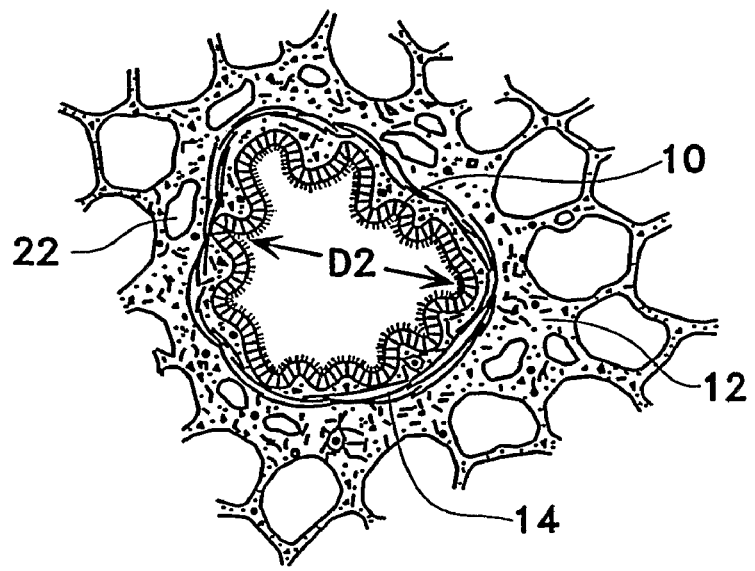
FIG. 2B is a cross sectional view of a bronchiole in a healthy patient.
Figure 3:
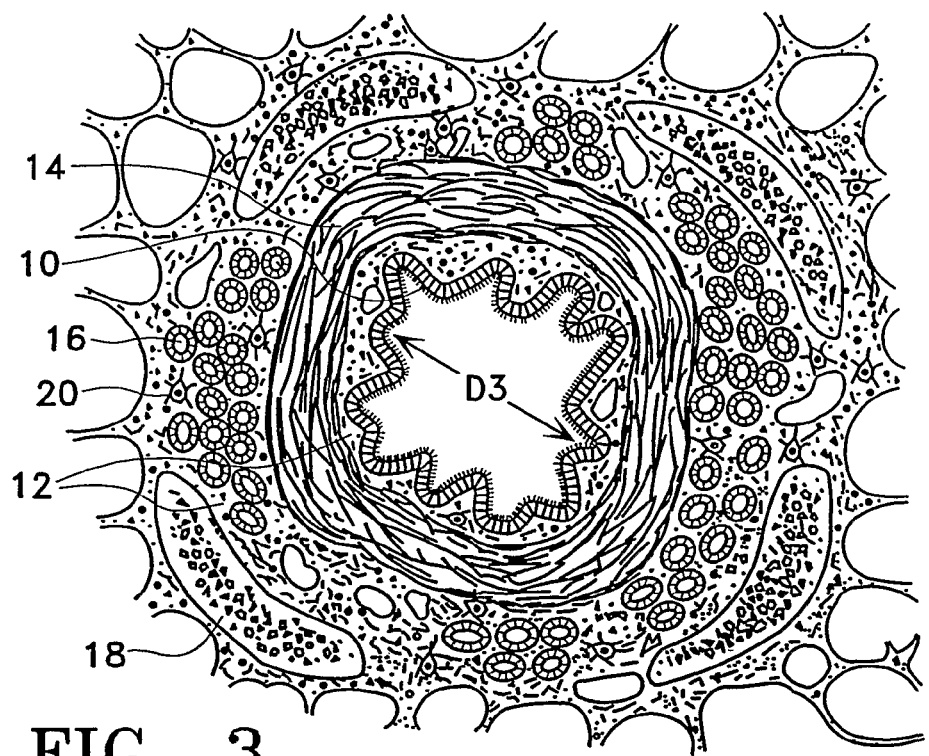
FIG. 3 is a cross sectional view of the bronchus of FIG. 2A showing the remodeling and constriction occurring in an asthma patient.

The present invention is particularly useful in treating lung tissue. This is surprising in view of the unique and complicated structure of lung tissue. Referring first to FIGS. 2A and 2B, a cross section of two different airways in a healthy patient is shown. The airway of FIG. 2A is a medium sized bronchus having an airway diameter D1 of about 3 mm. FIG. 2B shows a section through a bronchiole having an airway diameter D2 of about 1.5 mm. Each airway includes a folded inner surface or epithelium 10 surrounded by stroma 12 and smooth muscle tissue 14. The larger airways including the bronchus shown in FIG. 2A also have mucous glands 16 and cartilage 18 surrounding the smooth muscle tissue 14. Nerve fibers 20 and blood vessels 24 surround the airway. The airway is thus quite different from other tissues such as blood vessel tissue which does not include such folds, cartilage or mucous glands. In contrast, FIG. 3 illustrates the bronchus of FIG. 2A in which the smooth muscle 14 has hypertrophied and increased in thickness causing the airway diameter to be reduced from the diameter D1 to a diameter D3. Accordingly, the airways to be treated with the device of the present invention may be 1 mm in diameter or greater, more preferably 3 mm in diameter or greater.

Figure 4:
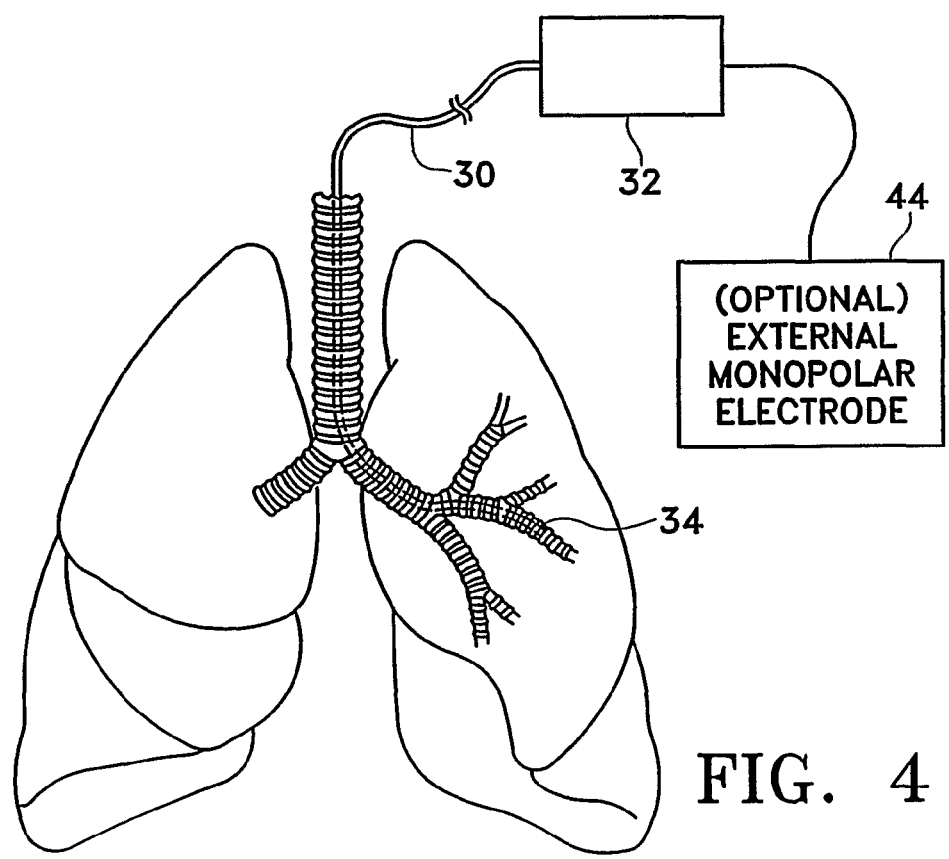
FIG. 4 is an illustration of the lungs being treated with a device and controller according to the present invention.

FIG. 4 is an illustration of the lungs being treated with a system 36 according to the present invention. The system 36 includes a controller 32 and an energy treatment device 30 which may be an elongated member as described further below. The device 30 also includes an expandable distal section which can be positioned at a treatment site 34 within a lung or another target medium. In operation, the device is manipulated to the treatment site 34. RF energy, for example, is delivered through the energy delivering device and penetrates the surface of the lung tissue such that tissue is affected below the epithelial layer as well as on the surface of the lung tissue.

Energy Delivering Device

As indicated above, the present invention includes a controller 32 and a device 30 through which it delivers energy to the target medium 34. A device 30 of the present invention should be of a size to access the bronchus or bronchioles of the human lung. The device may be sized to fit within bronchoscopes, preferably, with bronchoscopes having a working channel of 2 mm or less. The device may also include a steering member configured to guide the device to a desired target location. For example, this steering member may deflect a distal tip of the device in a desired direction to navigate to a desired bronchi or bronchiole.

The energy delivering apparatus 30 typically includes an elongate body having a proximal section and a distal section. The distal section features a radially expandable basket having a plurality of legs. The legs may be electrodes or have an active region defined by an insulated covering which contacts the medium to be treated. The basket is expanded with an actuator mechanism which may be provided in a handle attached to proximal end of the elongate body. Examples of energy delivering devices in accordance with the present invention are described in co-pending U.S. application Ser. No. 09/436,455 filed Nov. 8, 1999 which is hereby incorporated by reference in its entirety.

Temperature Sensor

The invention also includes a temperature detecting element. Examples of temperature detecting elements include thermocouples, infrared sensors, thermistors, resistance temperature detectors (RTDs), or any other apparatus capable of detecting temperatures or changes in temperature. The temperature detecting element is preferably placed in proximity to the expandable member.

Figure 5A:
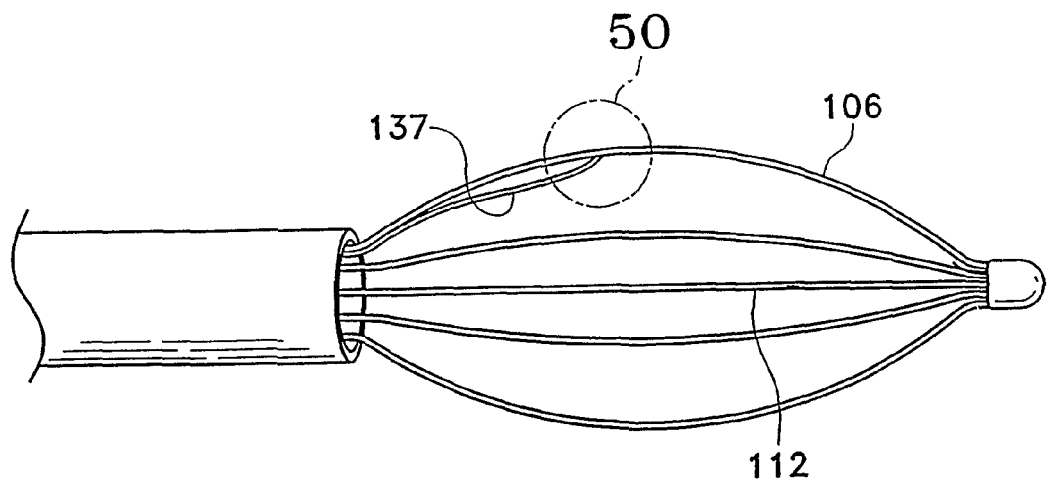
FIG. 5A is an illustration of an energy delivery device in accordance with the present invention.
Figure 5B:
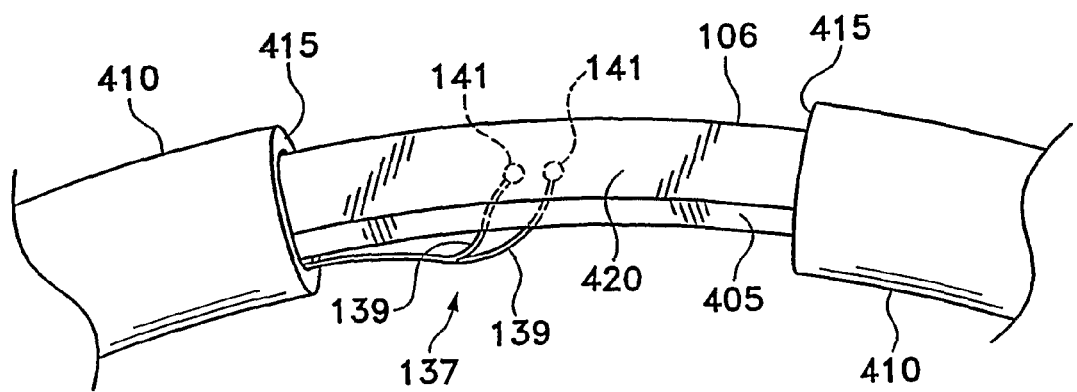
FIGS. 5B-5D show a partial view of a thermocouple attached to a basket leg in accordance with the present invention.

FIG. 5A is a partial view of a variation of the invention having thermocouple 137 positioned about midway along basket leg 106. FIG. 5B is an enlarged partial view of the thermocouple 137 of FIG. 5A showing the leads 139 separately coupled on an inwardly-facing surface of the leg 106. Consequently, the basket leg itself is used as part of the thermocouple junction upon which the temperature measurement is based. In other words, the thermocouple junction is intrinsic to the basket leg. This configuration is preferred because it provides an accurate temperature measurement of tissue contacting the leg 106 in the vicinity of the thermocouple leads. In contrast, typical thermocouple configurations consist of a thermocouple junction offset or extrinsic to the basket leg. We believe that thermocouple junctions having an offset from or extrinsic to the basket leg do not measure temperature as accurately in certain applications as thermocouple junctions which are intrinsic to the basket leg.

The leads 139 may be placed at other locations along the leg 106 including an edge 405. Joining the leads 139 to the edge 405, however, is undesirable because of its relatively small bonding surface.

FIG. 5B also shows basket leg 106 having an outer insulating material or coating 410. The boundaries 415 of the insulating material 410 define an uninsulated, active section of electrode leg 106 which delivers energy to the tissue walls. Preferably, the insulating coating 410 is heat shrink tubing or a polymeric coating. However, other insulating materials may be used.

Figure 5C:
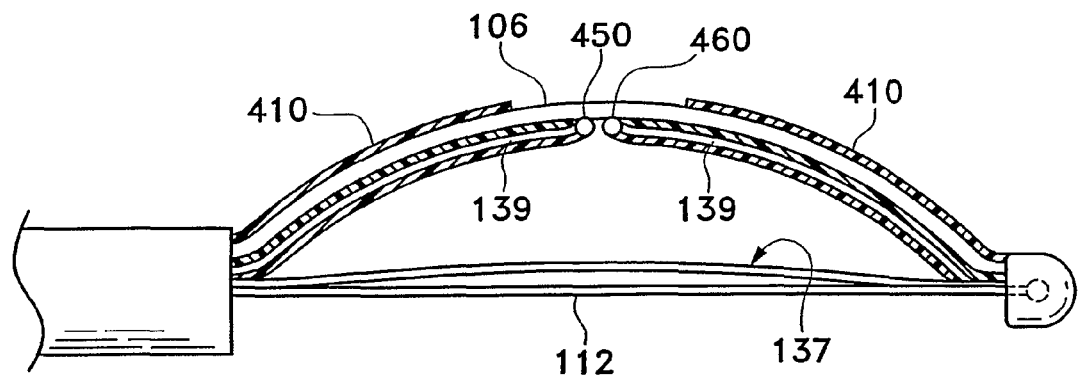
Figure 5D:
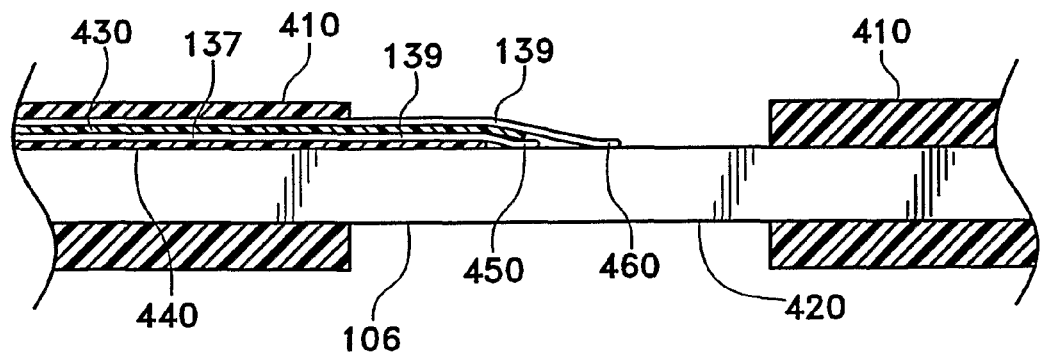

FIGS. 5C and 5D show another variation of the present invention having thin foil or laminated thermocouple leads 139. The thermocouple leads 139 are configured as foils or layers which can be, for example, prefabricated foils or sputtered films. Suitable materials for the thermocouple leads (listed in pairs) include, but are not limited to: Constantan and Copper; Constantan and Nickel-Chromium; Constantan and Iron; and Nickel-Aluminum and Nickel-Chromium. The thermocouple pair, CHROMEL and ALUMEL (both of which are registered trademarks of Hoskins Manufacturing) is preferred. CHROMEL and ALUMEL is a standard thermocouple pair and has been shown to be biocompatible and corrosion resistant in our applications. The thermocouple leads 139 may be placed such that each lead approaches the center of the basket leg from an opposite end of the basket leg. The leads 139 then terminate in bond joints 440 and 450. Alternatively, as shown in the configuration of FIG. 5D, both thermocouple leads 139 may run from the same end of the basket leg 106.

Preferably, insulating layers 430 and 440 are disposed between the thin film leads 139 and the basket leg 106. The insulating layers 430 and 440 electrically separate the leads 139 as well as electrically separate the leads from the leg 106. The insulating layers 430 and 440 limit the thermocouple junction to bond joints 450 and 460, which are optimally positioned on active region 420 of basket leg 106.

Controller

The present invention includes a controller which controls the energy to be delivered to the airways via an energy transfer device. The controller includes at least one of the novel features disclosed hereinafter and may also incorporate features in known RF energy controllers. An example of a RF generator which may be modified in accordance with the present invention is the FORCE™ 2 Generator manufactured by Valleylab, Boulder, Colo., U.S.A. Another suitable technique to generate and control RF energy is to modulate RF output of a RF power amplifier by feeding it a suitable control signal.

The controller and power supply is configured to deliver enough energy to produce a desired effect in the lung. The power supply should also be configured to deliver the energy for a sufficient duration such that the effect persists. This is accomplished by a time setting which may be entered into the power supply memory by a user.

The power supply or generator of the present invention can also employ a number of algorithms to adjust energy delivery, to compensate for device failures (such as thermocouple detachment), to compensate for improper use (such as poor contact of the electrodes), and to compensate for tissue inhomogeneities which can affect energy delivery such as, for example, subsurface vessels, adjacent airways, or variations in connective tissue.

The power supply can also include circuitry for monitoring parameters of energy transfer: (for example, voltage, current, power, impedance, as well as temperature from the temperature sensing element), and use this information to control the amount of energy delivered. In the case of delivering RF energy, typical frequencies of the RF energy or RF power waveform are from 300 to 1750 kHz with 300 to 500 kHz or 450 to 475 being preferred. The RF power-level generally ranges from about 0-30 W but depends upon a number of factors such as, size of the electrodes. The controller may also be configured to independently and selectively apply energy to one or more of the basket leg electrodes.

A power supply may also include control modes for delivering energy safely and effectively. Energy may be delivered in open loop (power held constant) mode for a specific time duration. Energy may also be delivered in temperature control mode, with output power varied to maintain a certain temperature for a specific time duration. In the case of RF energy delivery via RF electrodes, the power supply may also operate in impedance control mode.

Temperature Control Mode

In a temperature control mode, the power supply may operate up to a 75° C. setting. That is, the temperature measured by the thermocouple can reach up to 75° C. before the power supply is shut off. The duration must be long enough to produce the desired effect, but as short as possible to allow treatment of all of the desired target airways within a lung. For example, up to 15 seconds is suitable, and more preferably 8 to 12 seconds with about 10 seconds per activation (while the device is stationary) being preferred. Shorter duration with higher temperature will also produce an acceptable acute effect.

It should be noted that different device constructions utilize different parameter settings to achieve the desired effect. For example, while direct RF electrodes typically utilize temperatures up to 75° C. in temperature control mode, resistively heated electrodes may utilize temperatures up to 90° C.

Energy Pulses and Energy Modulation

Short bursts or pulses of RF energy may also be delivered to the target tissue. Short pulses of RF energy heat the proximal tissue while the deeper tissue, which is primarily heated by conduction through the proximal tissue, cools between the bursts of energy. Short pulses of energy therefore tend to isolate treatment to the proximal tissue.

The application of short pulses of RF energy may be accomplished by modulating the RF power waveform with a modulation waveform. Modulating the RF power waveform may be performed while employing any of the other control algorithms discussed herein so long as they are not exclusive of one another. For example, the RF energy may be modulated while in a temperature control mode.

Examples of modulation waveforms include but are not limited to a pulse train of square waves, sinusoidal, or any other waveform types. In the case of square wave modulation, the modulated RF energy can be characterized in terms of a pulse width (the time of an individual pulse of RF energy) and a duty cycle (the percent of time the RF output is applied). A suitable duty cycle can be up to 100% which is essentially applying RF energy without modulation. Duty cycles up to 80% or up to 50% may also be suitable for limiting collateral damage or to localize the affect of the applied energy.

Feedback Algorithm

As indicated above, the present invention includes controllers having various algorithms. The algorithms may be either analog and digital based. A preferred embodiment is a three parameter controller, or Proportional-Integral-Derivative (PID) controller which employs the following algorithm: $P_{i+1}=P_i+G(\alpha e_i+\beta e_{i-1}+\gamma e_{i-2})$ where $P_{i+1}$ is a new power set point, $P_i$ is a previous power set point, $\alpha$, $\beta$ and $\gamma$ are preset values, G is a variable gain factor and $e_i$, $e_{i-1}$, $e_{i-2}$ correspond to error at the present time step, error one step previous and error two steps previous where the error is the difference between the preset temperature and a measured temperature.

We have found that by using a variable gain factor (G) to adaptively control RF energy delivery, the system of the present invention can treat a wide range of tissue types including lung tissue bronchus, bronchioles and other airway passages. The variable gain factor scales the coefficients (alpha, beta, and gamma; each a function of the three PID parameters) based on, for example, the temperature response to energy input during the initial temperature ramp up.

Exemplary PID parameters are presented herein, expressed in alpha-beta-gamma space, for an energy delivering device and controller of the present invention. These settings and timings are based on testing in various animal lung tissues using an energy delivering apparatus as described above. First, the gain factor preferably varies and is reset 0.1 to 2 and more preferably at 0.5 seconds after energy delivery has begun. Preferably, the gain factor is reset as follows: G is reset to 0.9 to 1.0 and preferably 0.9 if a temperature rise in ° C. per Joule is less than or equal to 2.5; G is reset to 0.4 to 0.5 and preferably 0.5 if a temperature rise in ° C. per Joule is between 2.5 to 5.0; G is reset to 0.2 to 0.3 and preferably 0.2 if a temperature rise in ° C. per Joule is equal to 5.0 to 7.5; and G is reset to 0.1 to 0.2 and preferably 0.1 if a temperature rise in ° C. per Joule is greater than 7.5. We have also found that a suitable value for $\alpha$ is from 1 to 2; for $\beta$ is from −1 to −2; and for $\gamma$ is from −0.5 to 0.5. More preferably $\alpha$, $\beta$, $\gamma$ are 1.6, −1.6, and 0.0 respectively.

It is also possible to change the relative weights of alpha, beta, and gamma depending upon monitored temperature response working in either PID or Alpha-Beta-Gamma coordinate space beyond just scaling the alpha-beta-gamma coefficients with a variable gain factor. This can be done by individually adjusting any or all of alpha, beta, or gamma.

In another variation of the present invention, the PID algorithm is $P_{i+1}=P_i+(G_1 e_i+G_2 e_{i-1}+G_3 e_{i-2})$ and $G_1$, $G_2$ and $G_3$ are each variable gain factors. The invention includes configuring the controller such that $G_1$, $G_2$ and $G_3$ are reset to 0.90 to 2.00, −0.90 to −2.00 and 0.50 to −0.50 respectively if a temperature rise in ° C. per Joule is less than or equal to 2.5; to 0.40 to 1.00, −0.40 to −1.00 and 0.25 to −0.25 respectively if a temperature rise in ° C. per Joule is between 2.5 to 5.0; to 0.20 to 0.60, −0.20 to −0.60 and 0.15 to −0.15 respectively if a temperature rise in ° C. per Joule is equal to 5.0 to 7.5; and to 0.10 to 0.40, −0.10 to −0.40 and 0.10 to −0.10 respectively if a temperature rise in ° C. per Joule is greater than 7.5. Each of the variable gain factors may be equal to a product of at least one preset value and at least one variable value.

It is also possible to employ an algorithm that continuously adapts to signals rather than at discrete sample steps, intervals or periods. The algorithm takes into account several variables upon which observed temperature response depends including, for example: initial temperature, time history of energy delivery, and the amount of energy required to maintain set point temperature. An exemplary analog PID algorithm is: $u=K_P e+K_I \int e\,dt+K_D(de/dt)$ where u is a signal to be adjusted such as, for example, a current, a voltage difference, or an output power which results in energy delivery from the electrode to the airway wall. $K_P$, $K_I$ and $K_D$ are preset or variable values which are multiplied with the proper error term where e(t) is the difference between a preset variable and a measured process variable such as temperature at time (t). The above equation is suitable for continuous and/or analog type controllers.

Power Shut Down Safety Algorithms

In addition to the control modes specified above, the power supply may include control algorithms to limit excessive thermal damage to the airway tissue. Damage may be limited by terminating or shutting down the energy being delivered to the target medium. The algorithms can be based on the expectation that the sensed temperature of the tissue will respond upon the application of energy. The temperature response, for example, may be a change in temperature in a specified time or the rate of change of temperature. The expected temperature response can be predicted as a function of the initially sensed temperature, the temperature data for a specified power level as a function of time, or any other variables found to affect tissue properties. The expected temperature response may thus be used as a parameter in a power supply safety algorithm. For example, if the measured temperature response is not within a predefined range of the expected temperature response, the power supply will automatically shut down.

Other control algorithms may also be employed. For example, an algorithm may be employed to shut down energy delivery if the sensed temperature does not rise by a certain number of degrees in a pre-specified amount of time after energy delivery begins. Preferably, if the sensed temperature does not increase more than about 10° C. in about 3 seconds, the power supply is shut off. More preferably, if the sensed temperature does not increase more than about 10° C. in about 1 second, the power supply is shut off.

Another way to stop energy delivery includes shutting down a power supply if the temperature ramp is not within a predefined range at any time during energy delivery. For example, if the measured rate of temperature change does not reach a predefined value, the power supply will stop delivery of the RF energy. The predefined values are predetermined and based on empirical data. Generally, the predefined values are based on the duration of time RF energy is delivered and the power-level applied. A suitable predefined rate of temperature change to stop energy delivery is from 8° C./second to 15° C./second in the first 5 seconds (preferably in the first 2 seconds) of commencing energy delivery.

Other algorithms include shutting down a power supply if a maximum temperature setting is exceeded or shutting down a power supply if the sensed temperature suddenly changes, such a change includes either a drop or rise, this change may indicate failure of the temperature sensing element. For example, the generator or power supply may be programmed to shut off if the sensed temperature drops more than about 10° C. in about 0.1 to 1 seconds and more preferably in about 0.2 seconds.

In another configuration, the power is terminated when the measured temperature exceeds a pre-selected temperature or exceeds the set point temperature by a pre-selected amount. For example, when the set point is exceeded by 5 to 20° C., more preferably 15° C. the power will terminate.

In another configuration, power is terminated when the measured temperature (averaged over a time window) exceeds a pre-selected temperature. For example, power may be terminated when the measured temperature (averaged over 1 to 5 seconds and preferably averaged over 2 seconds) exceeds the preset temperature by a predetermined amount.

The predetermined amount is generally from 1 to 10° C. and preferably about 5° C. Suitable preset temperatures are from 60 to 80° C. and most preferably about 65° C. Accordingly, in one exemplary configuration, the power is stopped when the measured temperature (averaged over 2 seconds) exceeds 70° C.

In another configuration, the power is terminated when the amount of energy delivered exceeds a maximum amount. A suitable maximum amount is 120 Joules for an energy delivery apparatus delivering energy to the airways of lungs.

In another configuration, the power is shut down depending on an impedance measurement. The impedance is monitored across a treated area of tissue within the lung. Impedance may also be monitored at more than one site within the lungs. The measuring of impedance may be but is not necessarily performed by the same electrodes used to deliver the energy treatment to the tissue. The impedance may be measured as is known in the art and as taught in U.S. application Ser. No. 09/436,455 which is incorporated by reference in its entirety. Accordingly, in one variation of the present invention, the power is adjusted or shut off when a measured impedance drops below a preset impedance value. When using the energy delivering device of the present invention to treat airways, a suitable range for the preset impedance value is from 40 to 60 ohms and preferably about 50 ohms.

In another variation, the energy delivery apparatus is configured to deliver an amount of power up to a maximum power. The maximum power can be from 10 to 40 watts and preferably from 15 to 20 watts.

In yet another configuration, the power supply is configured to shut down if the power delivered exceeds a maximum power and the measured temperature drops by a critical temperature difference within a sampling period of time. A suitable maximum power is from 15 to 20 Watts and preferably about 17 watts. The sampling period of time generally ranges from 0.1 to 1.0 seconds and preferably is about 0.5 seconds. A suitable range for the critical temperature difference is about 2° C.

It is to be understood that any of the above algorithms and shut-down configurations may be combined in a single controller. However, algorithms having mutually exclusive functions may not be combined.

While the power supply or generator preferably includes or employs a microprocessor, the invention is not so limited. Other means known in the art may be employed. For example, the generator may be hardwired to run one or more of the above discussed algorithms.

The controller is preferably programmable and configured to receive and manipulate other signals than the examples provided above. For example, other useful sensors may provide input signals to the processor to be used in determining the power output for the next step. The treatment of an airway may also involve placing a visualization system such as an endoscope or bronchoscope into the airways. The treatment device is then inserted through or next to the bronchoscope or endoscope while visualizing the airways. Alternatively, the visualization system may be built directly into the treatment device using fiber optic imaging and lenses or a CCD and lens arranged at the distal portion of the treatment device. The treatment device may also be positioned using radiographic visualization such as fluoroscopy or other external visualization means.

EXAMPLES

A system to treat airways in accordance with the present invention was built and tested in vivo on two canines. The system included an energy delivering apparatus having a distal basket. The basket included electrode legs and a temperature sensor mounted to one of the legs. The system also included a generator programmed to measure the temperature change per energy unit during the first half-second of treatment. A PID gain factor was adjusted depending on the measured tissue response. That is, the gain factor was adjusted based on the temperature change per joule output during the first half second. In general, this corresponds to a higher gain for less responsive tissue and lower gain for more responsive tissue.

After treating the test subjects with a general anesthetic, RF energy was delivered to target regions using an energy delivery device and generator as described above. In particular, energy activations were performed on all available intraparenchymal airways three millimeters or larger in diameter in both lungs. Three hundred sixty-three activations using a 65° C. temperature setting were performed in the two animals (i.e., 180 activations per animal). Additionally, in twenty of the activations in each animal, the energy delivery device was deliberately deployed improperly to provide a "Stress" condition.

In each activation, the measured temperature reached and stabilized at 65° C. or, in the case of the twenty activations under "stress" conditions, the power properly shut off. Thus, the present invention can successfully treat lung tissue with a variable gain setting and various safety algorithms to safely maintain a preset temperature at the electrode or lung tissue surface. This temperature control is particularly advantageous when treating the airways of lungs to reduce asthma symptoms.

This invention has been described and specific embodiments or examples of the invention have been portrayed to convey a proper understanding of the invention. The use of such examples is not intended to limit the invention in any way. Additionally, to the extent that there are variations of the invention which are within the spirit of the disclosure and are equivalent to features found in the claims, it is the intent that the claims cover those variations as well. All equivalents are considered to be within the scope of the claimed invention, even those which may not have been set forth herein merely for the sake of brevity. Also, the various aspects of the invention described herein may be modified and/or used in combination with such other aspects also described to be part of the invention either explicitly or inherently to form other advantageous variations considered to be part of the invention covered by the claims which follow.

The invention described herein expressly incorporates the following co-pending applications by reference in their entirety: U.S. application Ser. Nos. 09/095,323; 09/095,323; 09/349,715; 09/296,040; 09/436,455; and U.S. application Ser. No. 09/535,856.

The invention claimed is:

1. A method for treating a lung by transferring energy from an active region of an energy delivery apparatus to an airway wall of said lung, said energy delivery apparatus having a flexible elongate body and a distal section and said active region being located in said distal section, said energy delivery apparatus further having a temperature sensor located in said distal section for measuring a temperature ($T_M$) of said airway wall, said method comprising:

setting a preset temperature ($T_s$);

determining a power set point ($P_i$) to deliver energy from said active region to said target medium;

measuring said $T_M$ using said temperature sensor;

determining a new power set point ($P_i+_1$) based on an error (e) between said preset temperature ($T_s$) and said measured temperature ($T_M$) using a PID algorithm; and terminating said energy delivery when the temperature does not rise a predetermined amount in a specified period of time.

2. The process of claim 1 comprising terminating said energy delivery if said energy delivered exceeds a maximum energy.

3. The process of claim 2 wherein said maximum energy is 120 joules.

4. The process of claim 1 further comprising measuring impedance and terminating said energy delivery when said impedance, drops below a preset impedance value.

5. The process of claim 4 wherein said preset impedance value is from 40 to 60 ohms.

6. The process of claim 1 comprising terminating said energy delivery if said $T_M$ exceeds $T_s$ by a pre-selected value.

7. The process of claim 6 wherein said pre-selected value is 10° C.

8. The process of claim 6 wherein said pre-selected value is 15° C.

9. The process of claim 6 wherein said pre-selected value is 20° C.

10. The process of claim 1 wherein said delivering energy to a target medium is performed by delivering energy to an airway wall of a lung in vivo.

11. The process of claim 1 wherein the power is terminated when the temperature does not rise by more than about 10° C. in about 3 seconds.

12. The process of claim 1 wherein the power is terminated when the temperature does not rise by more than about 10° C. in about 1 second.

13. A process for transferring energy to a target medium using an energy delivery apparatus, said energy delivery apparatus having a flexible elongate body and a distal section wherein said distal section includes an expandable basket with at least one active region for transferring energy to said target medium, said energy delivery apparatus further having a temperature sensor located in said distal section for measuring a temperature ($T_M$) of said target medium, said process comprising:

setting a preset temperature ($T_s$);

determining a power set point ($P_i$) to deliver energy from said active region to said target medium;

measuring said $T_M$ using said temperature sensor;

determining a new power set point ($P_i+_1$) based on an error (e) between said preset temperature ($T_s$) and said measured temperature ($T_M$) using an algorithm having a variable gain factor, wherein said algorithm is:

$P_{i+1} = P_i + G(\alpha e_i + \beta e_{i-1} + \gamma e_{i-2})$ where $\alpha$, $\beta$ and $\gamma$ are preset values, and wherein at least one of $\alpha$, $\beta$ and $\gamma$ is from −0.5 to 0.5.

14. The process of claim 13 wherein the algorithm further includes a gain factor (G).

15. The process of claim 14 comprising resetting G 0.1 to 2 seconds after energy delivery has begun.

16. The process of claim 15 comprising resetting G 0.5 seconds after energy delivery has begun.

17. The process of claim 16 comprising resetting G to 0.9 to 1.0 if a temperature rise in ° C. per Joule is less than or equal to 2.5.

18. The process of claim 16 comprising resetting G to 0.4 to 0.5 if a temperature rise in ° C. per Joule is between 2.5 to 5.0.

19. The process of claim 16 comprising resetting G to 0.2 to 0.3 if a temperature rise in ° C. per Joule is equal to 5.0 to 7.5.

20. The process of claim 16 comprising resetting G to 0.1 to 0.2 if a temperature rise in ° C. per Joule is greater than 7.5.

21. The process of claim 13 comprising setting $\alpha$ between 1 and 2.

22. The process of claim 21 comprising setting $\beta$ between −1 to −2.

23. The process of claim 13 comprising setting $\alpha$, $\beta$, $\gamma$ to 1.6, −1.6, and 0.0 respectively.

24. The process of claim 13 wherein energy is delivered for an activation period.

25. The process of claim 24 wherein said activation period up to 15 seconds.

26. The process of claim 25 wherein said activation period is 8 to 12 seconds.

27. The process of claim 26 wherein said activation period is 10 seconds.

28. The process of claim 13 comprising setting $T_s$ at a value between 60 to 80° C.

29. The process of claim 28 comprising setting $T_s$ at 65° C.

30. The process of claim 13 wherein said delivering energy to a target medium is performed by delivering energy to an airway wall of an excised lung.

31. The process of claim 13 wherein said delivering energy to a target medium is performed by delivering energy to a sponge or towel.

32. The process of claim 13 wherein the energy delivery apparatus is configured to deliver an amount of power up to a maximum power.

33. The process of claim 32 wherein the maximum power is 10 to 40 watts.

34. The process of claim 33 wherein the maximum power is 15 to 20 watts.

35. A process for transferring energy to a target medium using an energy delivery apparatus, said energy delivery apparatus having a flexible elongate body and a distal section wherein said distal section includes an expandable basket with at least one active region for transferring energy to said target medium, said energy delivery apparatus further having a temperature sensor located in said distal section for measuring a temperature ($T_M$) of said target medium, said process comprising:

setting a preset ($T_s$);

determining a power set point ($P_i$) to deliver energy from said active region to said target medium;

measuring said $T_M$ using said temperature sensor;

determining a new power set point ($P_i+_1$) based on an error (e) between said preset temperature ($T_s$) and said measured temperature($T_M$) using an algorithm having a variable gain factor; and terminating said energy delivery if an output power is greater or equal to a nominal output power and said $T_M$ drops by a critical temperature difference within a sampling period.

36. The process of claim 35 wherein said nominal output power is set at a value of at least 17 watts.

37. The process of claim 36 wherein said sampling period is set at a value of at least 0.5 seconds.

38. The process of claim 37 wherein said critical temperature difference is 2° C.

39. A process for transferring energy to a target medium using an energy delivery apparatus, said energy delivery apparatus having a flexible elongate body and a distal section wherein said distal section includes an expandable basket with at least one active region for transferring energy to said target medium, said energy delivery apparatus further having a temperature sensor located in said distal section for measuring a temperature ($T_M$) of said target medium, said process comprising:

setting a preset($T_s$);

determining a power set point ($P_i$) to deliver energy from said active region to said target medium;

measuring said $T_M$ using said temperature sensor;

determining a new power set point ($P_i+_1$) based on an error (e) between said preset temperature ($T_S$) and said measured temperature ($T_M$) using an algorithm having a variable gain factor: and terminating said energy delivery if said $T_M$ averaged over a time window exceeds $T_S$ by a fixed temperature difference.

40. The process of claim 39 wherein said fixed temperature difference is a value between 1 and 10° C.

41. The process of claim 40 wherein said fixed temperature difference is 5° C.

42. The process of claim 41 wherein said time window is between 1 and 5 seconds.

43. The process of claim 42 wherein said time window is 2 seconds.

44. A process for transferring energy to a target medium using an energy delivery apparatus, said energy delivery apparatus having a flexible elongate body and a distal section wherein said distal section includes an expandable basket with at least one active region for transferring energy to said target medium, said energy delivery apparatus further having a temperature sensor located in said distal section for measuring a temperature ($T_M$) of said target medium, said process comprising:

setting temperature ($T_s$);

determining a power set point ($P_i$) to deliver energy from said active region to said target medium;

measuring said $T_M$ using said temperature sensor;

determining a new power set point ($P_i+_1$) based on an error (e) between said preset temperature ($T_s$) and said measured temperature ($T_M$) using an algorithm having a variable gain factor; and wherein said algorithm is $P_{i+1}=P_i+(G_1e_i+G_2e_{i-1}+G_3e_{i-2})$ where $G_1$, $G_2$ and $G_3$ are variable gain factors.

45. The process of claim 44 wherein said controller is configured such that said variable gain factors are reset 0.1 to 2 seconds after energy delivery has begun.

46. The process of claim 45 wherein said controller is configured such that said variable gain factors are reset 0.5 seconds after energy delivery has begun.

47. The process of claim 46 wherein said controller is configured such that $G_1$, $G_2$ and $G_3$ are reset to 0.90 to 2.00, −0.90 to −2.00 and 0.50 to −0.50 respectively if a temperature rise in ° C. per Joule is less than or equal to 2.5.

48. The process of claim 46 wherein said controller is configured such that $G_1$, $G_2$ and $G_3$ are reset to 0.40 to 1.00, −0.40 to −1.00 and 0.25 to −0.25 respectively if a temperature rise in ° C. per Joule is between 2.5 to 5.0.

49. The process of claim 46 wherein said controller is configured such that $G_1$, $G_2$ and $G_3$ are reset to 0.20 to 0.60, −0.20 to −0.60 and 0.15 to −0.15 respectively if a temperature rise in ° C. per Joule is equal to 5.0 to 7.5.

50. The process of claim 46 wherein said controller is configured such that G1, G2 and G3 are reset to 0.10 to 0.40, −0.10 to −0.40 and 0.10 to −0.10 respectively if a temperature rise in ° C. per Joule is greater than 7.5.

51. The process of claim 46 wherein each of said variable gain factors is equal to a product of at least one preset value and at least one variable value.

52. A method for treating a lung by transferring energy from an active region of an energy delivery apparatus to an airway wall of said lung, said energy delivery apparatus having a flexible elongate body and a distal section and said active region being located in said distal section, said energy delivery apparatus further having a temperature sensor located in said distal section for measuring a temperature ($T_M$) of said airway wall, said method comprising:

setting a preset temperature ($T_s$);

determining a power set point ($P_i$) to deliver energy from said active region to said target medium;

delivering energy from the energy delivery apparatus to the airway wall during an energy delivery phase;

measuring said $T_M$ using said temperature sensor;

determining a new power set point ($P_i+_1$) based on an error (e) between said preset temperature ($T_s$) and said measured temperature ($T_M$) using a PID algorithm; and terminating said energy delivery when the temperature ramp rate is not within a predetermined range at a selected portion of the energy delivery phase.

53. The method of claim 52 wherein the temperature ramp rate is 8-15° C. for the first 2-5 seconds of the energy delivery phase.

* * * * *

UNITED STATES PATENT AND TRADEMARK OFFICE
CERTIFICATE OF CORRECTION

| | | |
|---|---|---|
| PATENT NO. | : 7,837,679 B2 | Page 1 of 2 |
| APPLICATION NO. | : 11/458084 | |
| DATED | : November 23, 2010 | |
| INVENTOR(S) | : Biggs et al. | |

It is certified that error appears in the above-identified patent and that said Letters Patent is hereby corrected as shown below:

On page 6, under "Other Publications", in column 2, line 39, delete "perisstent" and insert -- persistent --, therefor.

In column 13, line 52, in Claim 13, delete "$P_{i\,+1}$" and insert -- $P_{i+1}$ --, therefor.

In column 13, line 59, in Claim 15, delete "2seconds" and insert -- 2 seconds --, therefor.

In column 14, line 45, in Claim 35, after "preset" insert -- temperature --.

In column 15, line 5, in Claim 39, delete "preset($T_s$);" and insert -- preset temperature ($T_s$); --, therefor.

In column 15, line 12, in Claim 39, delete "factor:" and insert -- factor; --, therefor.

In column 15, line 22, in Claim 42, delete "1and" and insert -- 1 and --, therefor.

In column 15, line 24, in Claim 43, delete "2seconds." and insert -- 2 seconds. --, therefor.

In column 15, line 34, in Claim 44, after "setting" insert -- a preset --.

In column 16, line 6, in Claim 47, delete "-0.50respectively" and insert -- -0.50 respectively --, therefor.

In column 16, line 10, in Claim 48, delete "-0.25respectively" and insert -- -0.25 respectively --, therefor.

In column 16, line 14, in Claim 49, delete "-0.15respectively" and insert -- -0.15 respectively --, therefor.

In column 16, line 18, in Claim 50, delete "-0.10respectively" and insert -- -0.10 respectively --, Signed and Sealed this
Twelfth Day of April, 2011

David J. Kappos
*Director of the United States Patent and Trademark Office*

CERTIFICATE OF CORRECTION (continued)
U.S. Pat. No. 7,837,679 B2 therefor.